US005859017A

United States Patent [19]
Eiseman et al.

[11] Patent Number: 5,859,017
[45] Date of Patent: Jan. 12, 1999

[54] METHOD FOR INHIBITING MAST CELL AND BASOPHIL ACTIVATION

[75] Inventors: Elisa Eiseman; Emer Clarke; Jack W. Singer, all of Seattle; Stuart L. Bursten, Snoqualmie, all of Wash.

[73] Assignee: Cell Therapeutics, Inc., Seattle, Wash.

[21] Appl. No.: 221,814

[22] Filed: Apr. 1, 1994

[51] Int. Cl.$^6$ .................. A61K 31/52; A61K 31/445; A61K 31/505; A61K 31/08

[52] U.S. Cl. .................. 514/263; 514/315; 514/249; 514/259; 514/265; 514/274; 514/312; 514/418; 514/588; 514/617; 514/627; 514/671; 514/690; 514/720; 514/723

[58] Field of Search .................. 514/315, 249, 514/259, 263, 265, 274, 312, 418, 588, 617, 627, 671, 690, 720, 723

[56] References Cited

U.S. PATENT DOCUMENTS

| | | | |
|---|---|---|---|
| 4,223,032 | 9/1980 | Buckle et al. | 424/258 |
| 4,912,092 | 3/1990 | Gruber | 514/45 |
| 4,940,782 | 7/1990 | Rup et al. | 530/387 |
| 5,000,936 | 3/1991 | Chibret | 424/43 |
| 5,134,119 | 7/1992 | Lezdey et al. | 514/8 |
| 5,354,756 | 10/1994 | Underiner et al. | 514/263 |

OTHER PUBLICATIONS

Burd et al., *J. Exp. Med.*, vol. 170, pp. 245–257, "Interleukin 3–Dependent and –Independent Mast Cells stimulated with IgE And antigens Express Multiple Cytokines", Jul. 1989.

Eiseman et al., *Nature*, vol. 355, pp. 78–80, "Engagement of the high–affinity IgE receptor activates src protein–related tyrosine kinases", Jan. 1992.

Gauchat et al., *Nature*, vol. 365, pp. 340–343, "Induction of human IgE synthesis in B Cells by mast cells and basophils", Sep. 1993.

Li et al., *Molecular and Cellular Biology*, vol. 12, No. 7, pp. 3176–3182, "FcεR1 –Medicated Tyrosine Phosphorylation of Multiple Proteins, Including Phospholipase Cγ1 and the Receptor βγ2 Complex, in RBL–2H3 Rat Basophilic Leukemia Cells", Jul. 1992.

Lin et al., *Biochem. J.*, vol. 287, pp. 325–331, "Phosphatidylcholine–specific phospholipase D–derived 1,2–diacylglycerol does not initiate protein kinase C activation in the RBL 2H3 mast–cell line", 1992.

Ozawa et al., *The Journal of Biological Chemistry*, vol. 268, No. 3, pp. 1749–1756, "$Ca^{2+}$–dependent and $Ca^{2+}$–independent Isozymes of Protein Kinase C Mediate Exocytosis in Antigen–stimulated Rat Basophilic RBL–2H3 Cells", Jan. 1993.

Ozawa et al., *The Journal of Biological Chemistry*, vol. 268, No. 4, pp. 2280–2283, "Difference Isozymes of Protein Kinase C Mediate Feedback Inhibition of Phospholipase C and Stimulatory Signals for Exocytosis in Rat RBL–2H3 Cells", Feb. 1993.

Park et al., *The Journal of Biological Chemistry*, vol. 266, No. 36, pp. 24237–24240, "Ige–induced Tyrosine Phosphorylation of Phospholipase C–γ1 in Rat Basophilic Leukemia Cells", Dec. 1991.

Plaut et al., *Nature*, vol. 339, pp. 64–67, "Mast cell lines produce lymphokines in response to cross–linkage of FcεRI or to calcium ionophores", May 1989.

White et al., *The Journal of Immunology*, vol. 141, No. 2, pp. 942–946, "Translocation of Protein Kinase C In Rat Basophilic Leukemia Cells Induced By Phorbol Ester Or By Aggregation of IgE Receptors", Aug. 1988.

*Primary Examiner*—Deborah Lambkin
*Attorney, Agent, or Firm*—Stephen Faciszewski

[57] ABSTRACT

In a method for treating or preventing allergy or allergic disorders an effective amount of a compound that inhibits intracellular generation of phosphatidic acid and diacylglycerol is administered. The intracellular generation of phosphatidic acid and diacylglycerol results from allergen presentation or mast cell/basophil activation.

7 Claims, 17 Drawing Sheets

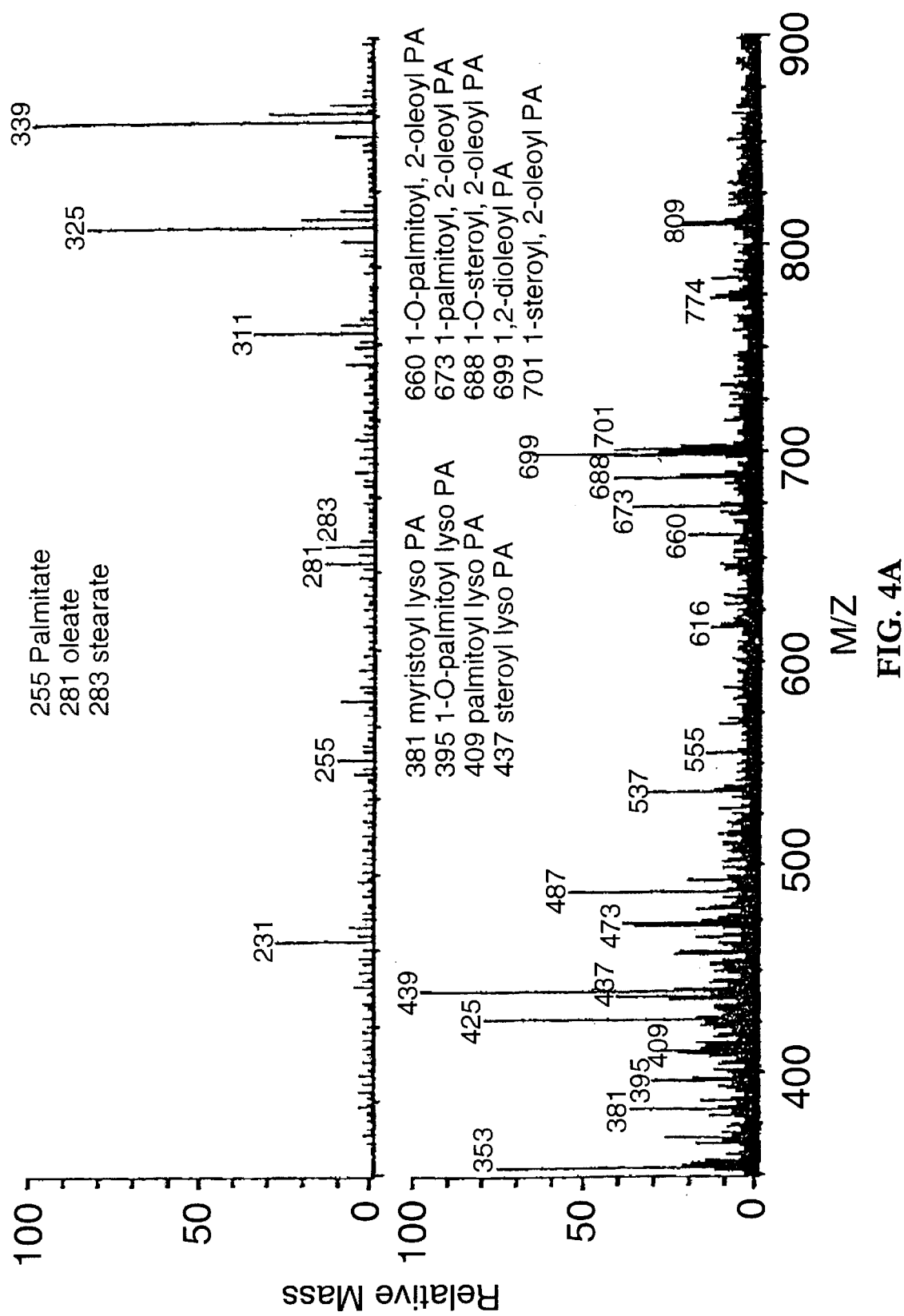

METHOD FOR INHIBITING MAST CELL AND BASOPHIL ACTIVATION

TECHNICAL FIELD OF THE INVENTION

The present invention provides a method for selective inhibition of an allergic and allergic response resulting from stimulation of mast cells through the high affinity IgE receptor, FcεRI. The method comprises administering a compound which inhibits signal transduction by inhibiting accumulation of relevant species of phosphatidic acid (PA) and diacyl glycerol (DAG) generated in response to an allergen primary stimulus acting through FcεRI on a mast cell or basophil.

BACKGROUND OF THE INVENTION

Allergic rhinitis is the sixth most common chronic condition in the United States, outranking heart disease. Between 5 and 22% of the United States population are estimated to have allergies—40 million people being a median estimate. Some allergy victims experience only mild and seasonal symptoms, yet others experience severe, almost continuous symptoms. Incidence of allergy is equally as common for either sex. Evidence predicts genetic predisposition to allergic disorders, such as, for example, asthma, rhinitis, urticaria, and eczema.

The allergic response is classified by three stages: 1) a sensitization stage; 2) an immediate hypersensitivity reaction; and 3) a late phase hypersensitivity reaction. Sensitization occurs when an allergen first enters the body. The allergen causes no overt symptoms, but instead it prepares the body to react promptly to future encounters with the allergen. During sensitization, macrophages phagocitize, process and present the allergen on their surface, activating helper T cells. Activated T cells produce interleukin-4 (IL-4), which is necessary for IgE production by B cells. IgE production also requires physical interaction of CD40, expressed on the surface of B cells, with CD40L, a CD40 ligand expressed on the surface of T cells.

IgE synthesized by B cells in response to initial exposure to allergen then binds to its high affinity receptor, FcεRI, which is expressed on the surface of mast cells and basophils, thus priming the body for its next encounter with allergen.

Subsequent contact with the allergen induces an immediate hypersensitive reaction. Allergen cross-links IgE bound to its receptor on mast cells, initiating activation of multiple kinases, which results in rapid changes in protein phosphorylation. Eiseman et al., *Nature*, vol. 355, 78–80 (1992) and Li et al., *Mol. Cell Biol.*, vol. 12, 3176–3182 (1992).

In one event triggered by this response, tyrosine phosphorylation of phospholipase Cγ1 (PLCγ1) increases hydrolysis of phosphatidylinositol to inositol triphosphates and DAG, in turn increasing intracellular levels of calcium, and activates protein kinase C (PKC). Park et al., *J Biol. Chem.*, vol. 266, 24237–24240 (1991).

Other enzymatic activities implicated as components of the allergic response include: hydrolysis of phosphatidylcholine (PC) to phosphatidic acid (PA) by phospholipase D (PLD); dephosphorylation of PA to DAG by phosphatidic acid phosphohydrolase (PAPH); activation of protein kinase C (PKC) by DAG; the release of arachadonic acid from phopholipids by phospholipase $A_2$ ($PLA_2$); metabolism of arachidonic acid by cyclooxygenase and lipoxynase to form prostaglandins and leukotreines; regulation of calcium influx by G proteins; and post-translational isoprenylation of proteins. This sequence of events ultimately results in degranulation, and the synthesis and secretion of prostaglandins and leukotreines. Lin et al., *Biochem J.*, vol. 287, 325–331 (1992) and Ozawa et al., *J. Biol. Chem.*, vol. 268, 1749–1756 (1993).

During the late phase hypersensitivity reaction, mast cells recruit, prime and activate other cells, such as neutophils, macrophages, basophils and eosinophils, by secreting cytokines and chemokines. Some cytokines that are produced, such as interleukin-3 (IL-3)—a mast cell growth factor-, IL-4(an IgE "switch factor"), IL-5 (an eosinophil differentiation factor), and interleukin-6 (IL-6)—a factor controlling immunoglobulin secretion, are known to be produced by a subset of T cells, Th2 cells. Other cytokines include interleukin-1(IL-1), tumor necrosis factor (TNFα), granulocyte macrophage-colony stimulating factor (GM-CSF), interferon-γ(INF-γ), JE, macrophage inhibitory peptide-1α (MIP1α) and macrophage inhibitory peptide-1 β(MIP1β). Plaut et al., *Nature*, vol. 339, 64–67 (1989) and Burd et al., *J Exp Med*, vol. 170, 245–257 (1989).

In addition to producing IL-4, mast cells and basophils also express the ligand (CD40L) to the CD40 receptor, permitting direct regulation of IgE production independent of T cells. Gauchat et al., *Nature*, vol. 365, 340–343 (1993). In turn, many of the cells recruited to the inflammation site produce their own cytokines as well as histamine-releasing factors, causing a corresponding release of histamine. Activating and recruiting additional inflammatory cells to the initial contact site escalates and prolongs the inflammatory response.

For one particularly prevelent disease, asthma, estimates predict that 4 to 5 percent of the population in the United States, approximately 10 million people, suffer from its symptoms. Inadequate asthma therapies have, in part contributed to increased morbidity and mortality associated with this disease. Statistically, allergic asthma accounts for 90% of all asthmatic conditions in victims under 16 years old, 70% of asthmatic conditions in victims under 30 years old, and 50% of asthmatic conditions in those over 30 years old.

Asthma is a chronic illness characterized by episodic coughing, wheezing, chest tightness, and dyspnea. Allergen such as, ozone and tobacco, microorganisms, exercise or stress are some of the many causes of asthma. Much like an allergic response, asthma has an early and late phase response. Acute symptoms of the early phase usually peak in 30 to 60 minutes and then resolve within a few hours, either spontaneously or with treatment. Inflammatory events of the late phase usually peak in 5 to 6 hours and last from several hours to several days.

In allergic asthma, as in an allergic response, allergen cross-links IgE receptors on mast cells, triggering an early phase, asthmatic response. Activated mast cells then release histamine and other inflammatory mediators. Some pathologic consequences of histamine and inflammatory mediator release are: impaired bronchial smooth muscle contraction, heightened vascular permeability, epithelial damage, and vasodilation. Clinically, the symptoms are bronchospasm, mucus secretion, and edema. The late phase response is characterized by infiltration of eosinophils, neutrophils, and other inflammatory cells, coupled with secretion of highly viscous mucus.

Approximately 50% of all adults with early phase, allergen response will have a late phase response. Thus, if an early phase response were inhibited, likelihood of a late phase response occurring would be severely diminished. The various early events in the allergic response (discussed above) have therefore been of significant interest in investigations aimed at finding therapies that would inhibit or prevent both an early and late phase response.

Research has shown that an immediate consequence of IgE-primed FcεRI engagement by allergen on mast cells results in signal transduction through a second messenger pathway. The inventive method for inhibiting an allergic response makes use of compounds that inhibit allergen-stimulated FcεRI signal transduction.

SUMMARY OF THE INVENTION

The inventive method is a method for treating or preventing allergy or allergic disorders, in which an effective amount of a compound to inhibit intracellular generation of PA and DAG is administered to a subject having the allergy or allergic disorder. Relevant species of PA and DAG which are inhibited in the inventive method, include PA and DAG species having oleate-, arachidonate-, palmitate-, myristate-, and/or stearate-containing acyl moieties.

Specifically, the inventive method is a method for preventing or treating an allergic response by inhibiting, for example, degranulation and prostaglandin production through inhibition of relevant species of PA and DAG. These relevant species of PA and DAG play an important role in translating a signal initiated on the surface of mast cells and basophils through the IgE-primed FcεRI receptor by an allergen. This signal translation through relevant PA and DAG species results in degranulation, prostaglandin and leukotriene production, having deleterious results in the allergic response. Inhibition of these relevant species of PA and DAG prevents degranulation and production of prostaglandin, thus inhibiting activation of mast cells and basophils, and ultimately, undesirable effects of the allergen response.

Although any compound that is capable of inhibiting generation of these specific species of PA and DAG may be useful in the inventive method, preferred compounds will inhibit PA and DAG without interfering in allergen binding to the FcεRI receptor.

BRIEF DESCRIPTION OF THE DRAWINGS

FIGS. 4A–4E are mass spectra corresponding to HPLC or TLC fractions of relevant PA or DAG peaks generated in response to allergen stimulus.

DETAILED DESCRIPTION OF PREFERRED EMBODIMENTS

Figure 1A:
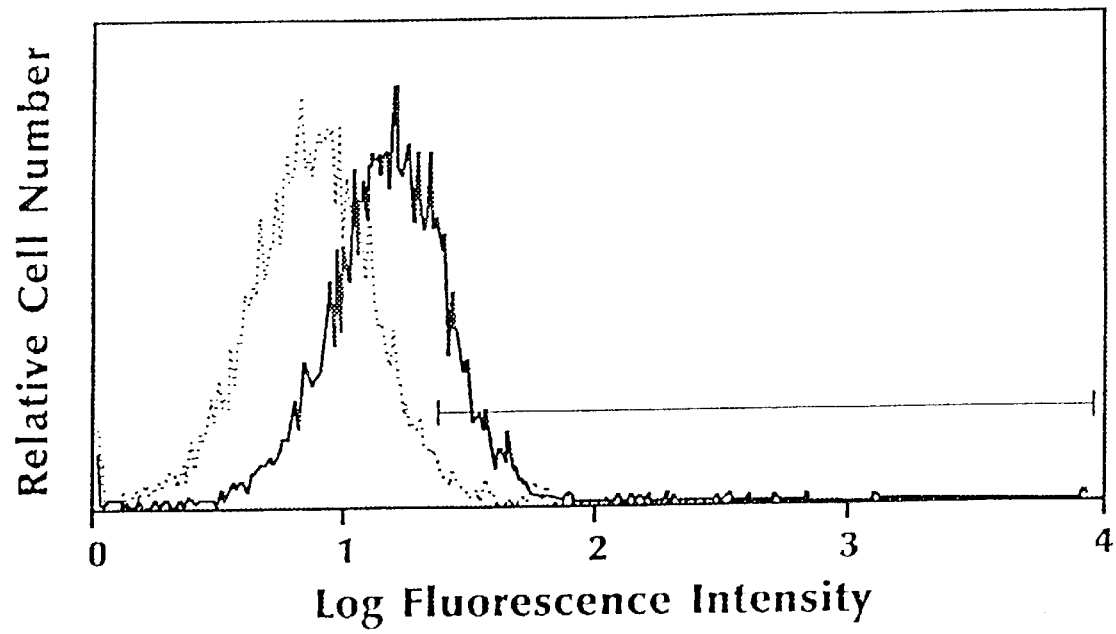
FIGS. 1A and 1B are flow cytometry spectra representing level of expression of the IgE high affinity receptor FcεRI on two cell lines, bone marrow-derived mast cells (BMMC) and an IL-3 dependent murine mast cells PT-18, respectively.

The inventive method uses inhibitors of FcεRI-stimulated PA and DAG accumulation in mast cells and basophils. By inhibiting species of PA and DAG resulting from mast cell and basophil activation by allergin, the inventive method inhibit degranulation measured by a $^3$H-serotonin assay and prostaglandin E2 (PGE2) production in primary murine bone marrow-derived mast cells (BMMC) and the rat basophilic leukemia cell line RBL-2H3 with IC50s of approximately 5–15μM. The use of these inhibitors shows that the production of PA and DAG is necessary for FcεRI-mediated signal transduction in mast cells.

Mechanism of Action

The inventive method permits treatment and prevention of an allergic response by inhibiting, for example, degranulation and ecosinoid production through inhibition of relevant species of PA and DAG, which are second messengers that play an important role in effecting the undesirable events of allergy. The inventive method accomplishes this by interfering with IgE signal transduction without affecting allergen binding to an IgE-primed FcεRI receptor. The inventive method, by inhibiting generation of FcεRI-stimulated PA and DAG interfere with FcεRI-induced degranulation and $PGE_2$ production. The relevant PA and DAG species are characterized by oleate-, arachidonate-, palmitate-, myristate-, and/or stearate-containing, sn-1 and sn-2 acyl groups.

The mechanism of IgE signal transduction leading to degranulation and ecosinoid production is thought to involve the induction of phospholipid second messenger PAs and DAGs having oleate-, arachidonate-, paimitate-, myristate-, and/or stearate-containing acyl moieties.

FcεRI-mediated activation induces phospholipid metabolism which leads to generation of relevant, identifiable species of PA and DAG. HPLC analysis of phospholipids confirms this result. As early as five seconds after antigen stimulation of cells, production of these phospholipids was observed. Mass spectroscopy analysis has revealed several species of PA and DAG present shortly (e.g. 15 seconds) after antigen stimulation. These species include, but are not limited to, 1-O-myristyl,2-myristyl; 1,2-dimyristoyl; 1-O-palmitoyl, 2oleoyl; 1palmitoyl, 2-stearoyl; 1-palmitoyl,2-oleoyl; 1-O-stearoyl,2-oleoyl; 1,2-dioleoyl; 1-stearoyl,2-arachidonyl;and 1-stearoyl,2-oleoyl; 1-stearoyl,2-oleoyl; 1-myristoyl,2-oleoyl; 1-myristoyl,2-palmitoyl; and 1-myristoyl,2-stearoyl PA and DAG.

Pre-incubation of cells bearing IgE-primed FcεRI receptors with a compound of the invention, prior to stimulation with a corresponding allergen, eliminates representative HPLC peaks previously shown to contain PA and DAG. Interference with the presence of these species of PA and DAG, observed in untreated cells, corresponds to inhibition of degranulation and prostaglandin production in mast cells and basophils.

The 1-stearoyl,2-arachidonyl PA is derived from phosphoinositol-4,5-bis phosphate ($PIP_2$) and the myristate-containing PA and DAG, especially the 1-O-myristoyl,2-myristoy PA, is derived from glycosyl-phosphatidylinostinol (GPI). "Late" (i.e., 5 minutes after activation) PA and DAG species have been reported to arise mainly from phosphatidyl choline (PC) by form PA by phosphatidyl-choline-specific phospholipase D (PC-PLD). The corresponding PA is then converted to DAG by phosphatidic acid phosphohydrolase (PAPH).

PKC activation plays an important role in FcεRI-mediated degranulation of mast cells and basophils. When mast cells are activated through FcεRI, PLC-γ1 is tyrosine phosphorylated and activated. Park et al., *J. Biol. Chem.*, vol. 266, 24237–24240(1991). This results in the hydrolysis of $PIP_2$ to form DAG. PKC is activated by DAG and translocates to the cell membrane. White et al., *J. Immunol.*, vol. 141, 942–947 (1988). This PKC activation in turn regulates PC-PLD activation to produce PA which is converted to DAG by PAPH. Lin et al., *Biochem. J.*, vol. 287, 325–331 (1992).

Ozawa et al. have reported that of the five isozymes expressed in the rat basophilic leukemia cell line RBL-2H3 PKC β and δ are necessary for degranulation. Ozawa et al., *J. Biol. Chem.*, vol. 268, 2280–2283(1993). In contrast, PKCα and εinhibit FcεRI-mediated $PIP_2$ hydrolysis by reducing the tyrosine phosphorylation of PLC-γ1. Ozawa et al. In addition, PKCαcan block FcεRI-mediated $PLA_2$ activation. The inventive method increases the amount of PKC activity in the cell membrane, as verified by PKC activity assays. These assays, discussed in the Examples, used rat basophilic leukemia cell line RBL-2H3. Western blots of PKC isoforms in RBL-2H3 cells using specific polyclonal anti-peptide antibodies confirm the presence of many isoforms of PKC, including PKCα, PKCβI, PKCβII, and PKCδ, PKCε, PKCζ. Since PKCα and PKCε are part of an apparent, important negative feedback mechanism in this system, an increased activation of PKCα and PKCε may likely inhibit PLC-γ1 activation. This would ultimately inhibit all of the downstream effects of FcεRI-mediated degranulation. Presence of these isoforms in in vitro analyses have been shown to inhibit degranulation. A pictoral representation of this sequence of events is presented below in Schematic A:

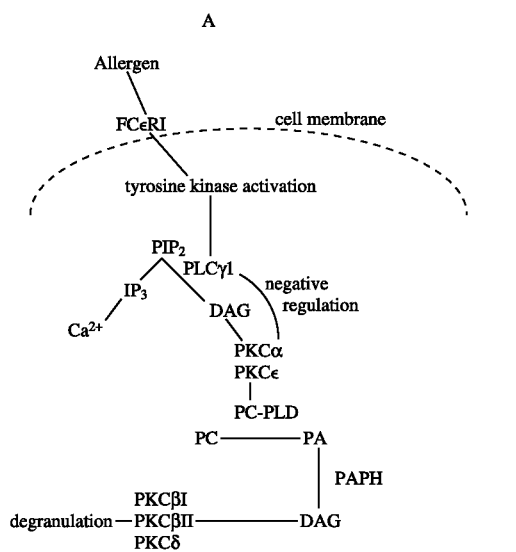

Compounds

Many compounds, as exemplified below, show activity for inhibiting PA and DAG production. These compounds specifically inhibit particular species of PA and DAG and do not interfering in allergen binding to the FcεRI receptor. These compounds are biochemically characterized by their ability to inhibit intracellular formation and accumulation of specific species of PA and DAG, which ultimately lead to degranulation and prostaglandin production in response to allergen. In the inventive method, the inhibitive compounds, a pharmaceutically acceptable salt, hydrate or solvate thereof, can be administered in a conventional dosage form to a human suffering from any of the described allergic conditions discussed.

The inventive method employs these small organic molecules, which can mimic binding to a complex of enzymes that mediate signal amplification and results in a diminution of intracellular PA levels (and corresponding levels of DAG) in response to the allergen stimulus.

Exemplary, preferred compounds according to the inventive method are selected from among compounds that exhibit activity for treating or preventing manifestations of allergy and allergic disorders, such as, for example, degranulation and prostaglandin and/or leukotriene production. These exemplary, preferred inhibitive compounds may be selected from the exemplary list of compounds below:

| No. | Chemical Name | Chemical Structure |
|---|---|---|
| 1101 | N-(5-hexenyl)phthalimide | 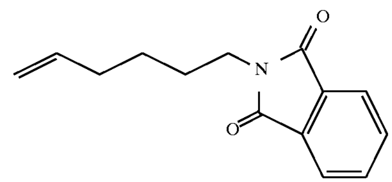 |
| 1102 | N-(8-nonenyl)phthalimide | 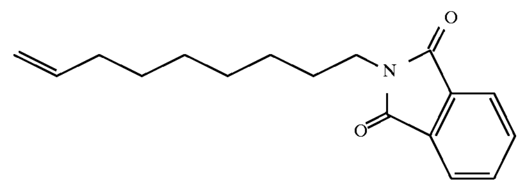 |
| 1107 | N-(10-undecenyl)phthalimide | 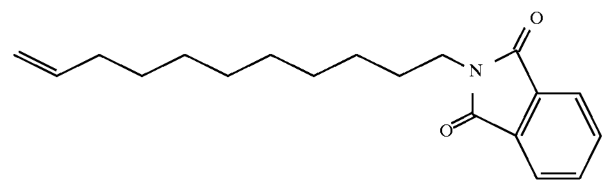 |
| 1110 | N-(5-Hexenyl)homophthalimide | 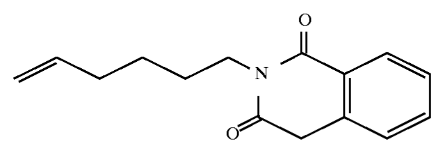 |
| 1112 | N-(10-Undecenyl)homophthalimide | 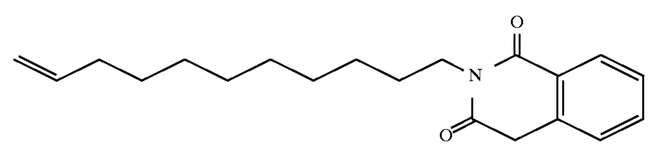 |
| 1203 | 1-(5-hexenyl)-3-methylbenzoyleneurea | 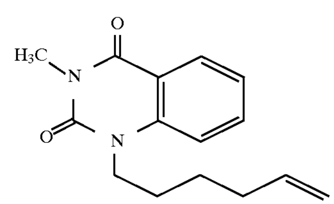 |

-continued

| No. | Chemical Name | Chemical Structure |
|---|---|---|
| 1210 | 1-(10-Undecenyl)-3-methylbenzoyleneurea | 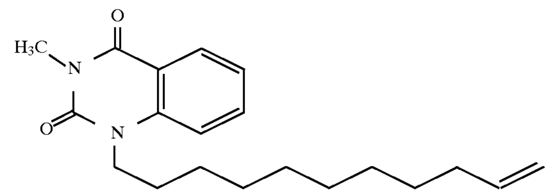 |
| 1211 | 3-(5-Hexenyl)benzoyleneurea | 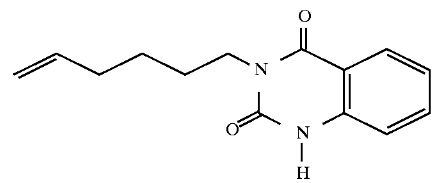 |
| 1212 | 3-(5-Hexenyl)-1-methylbenzoyleneurea | 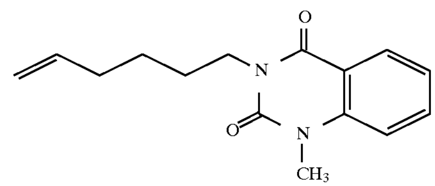 |
| 1213 | 3-(10-Undecenyl)-1-methylbenzoyleneurea | 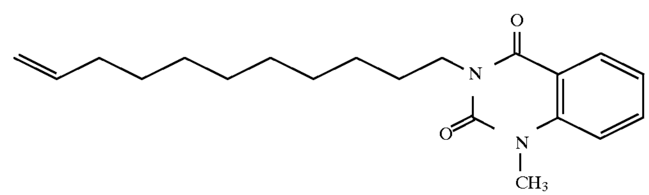 |
| 1214 | 3-(10-Undecenyl)quinazoline-4(3H)-one | 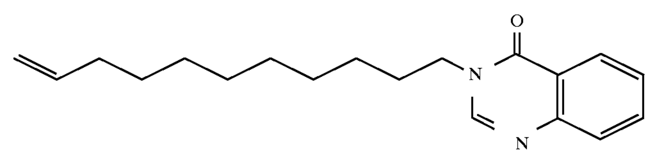 |
| 1305 | 1-dimethylamino-10-undecene | 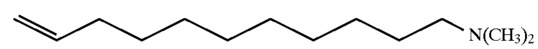 |

| No. | Chemical Name |
|---|---|
| 1307 | 1-(N-Methylacetamido)-10-undecene |
| 1319 | N-(10-Undecenyl)diacetamide |
| 1403 | 1-(10-undecenyl)-3-methyl-7-methylpivaloylxanthine |
| 1405 | 1-(8-nonenyl)-3-methylxanthine |
| 1406 | 1-(10-undecenyl)-3-methylxanthine |

-continued

| No. | Chemical Name | Chemical Structure |
|-----|---------------|--------------------|
| 1411 | 1-(8-nonenyl)-3-methyl-7-methylpivaloylxanthine | 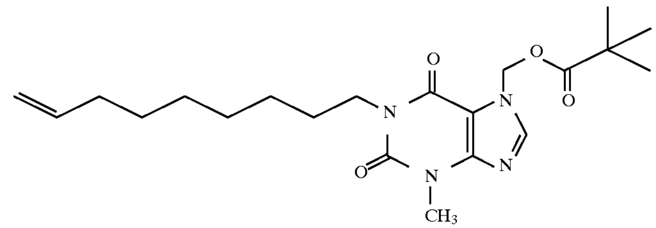 |
| 1418 | 7-(10-Undecenyl)-3-methylxanthine | 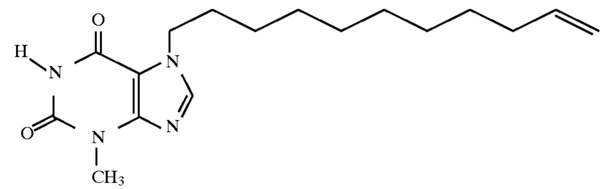 |
| 1420 | 7-(10-Undecenyl)-1,3-dimethyxanthine | 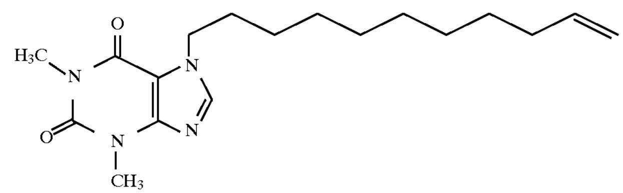 |
| 1421 | 3-(10-Undecenyl)-1-methyl-2,4-dioxotetrahydropteridine | 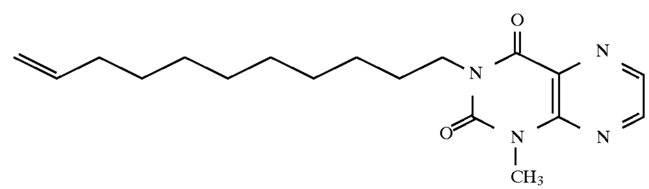 |
| 1438 | 1-(5-hexenyl)-3-methylxanthine | 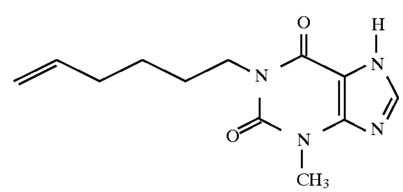 |

-continued

| No. | Chemical Name |
|---|---|
| 1441 | 1-(5-hexenyl)-3-methyl-7-methylpivaloylxanthine |
| 1442 | 1-(6-cis-nonenyl)-3-methylxanthine |
| 1508 | 1-(6-cis-nonenyl)-3,7-dimethylxanthine |
| 1524 | 1-(cis,cis-9,12-octadecadienyl)-3,7-dimethylxanthine |
| 1531 | 1-(2-propenyl)-3,7-dimethylxanthine |

| No. | Chemical Name | Chemical Structure |
|---|---|---|
| 1534 | 1-(6-heptenyl)-3,7-dimethylxanthine | 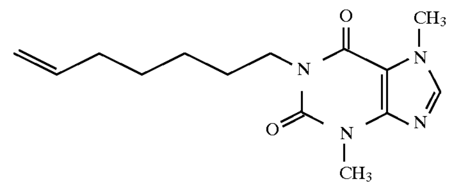 |
| 1535 | 1-(7-octenyl)-3,7-dimethylxanthine | 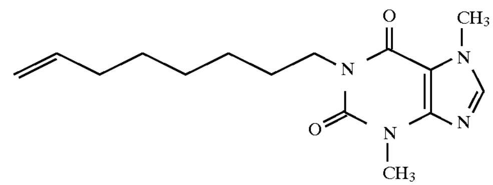 |
| 1539 | 1-(5-hexenyl)-3,7-dimethylxanthine | 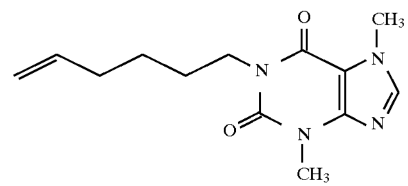 |
| 1550 | 1-(8-nonenyl)-3,7-dimethylxanthine | 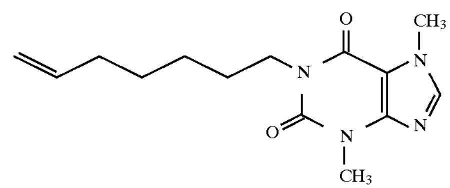 |
| 1563 | 1-(9,10-decenyl)-3,7-dimethylxanthine | 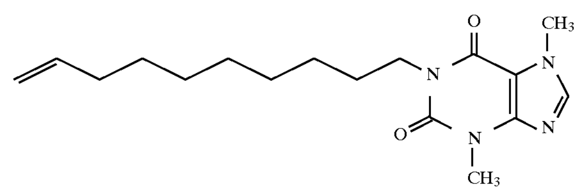 |

-continued

| No. | Chemical Name | Chemical Structure |
|---|---|---|
| 1575 | 1-(4-pentenyl)-3,7-dimethylxanthine | 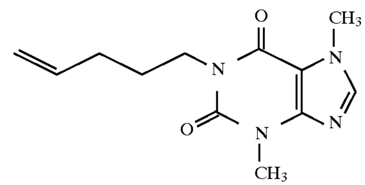 |
| 1579 | 1-(5-(3-methyl-2-butenoyl))hexyl-3,7-dimethylxanthine | 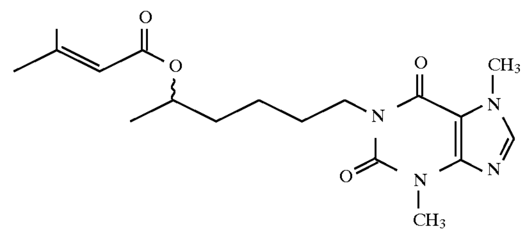 |
| 1581 | 1-(4-hexenyl)-3,7-dimethylxanthine | 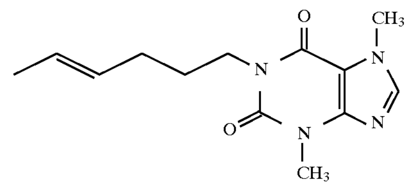 |
| 1596R | 1-(3-(R)-methyl-7-methyloct-6-enyl)-3,7-dimethylxanthine | 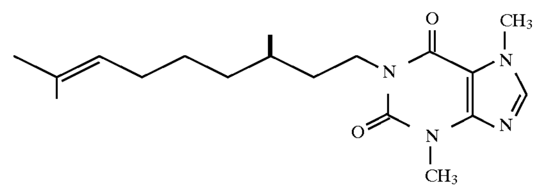 |
| 1596S | 1-(3-(S)-methyl-7-methyloct-6-enyl)-3,7-dimethylxanthine | 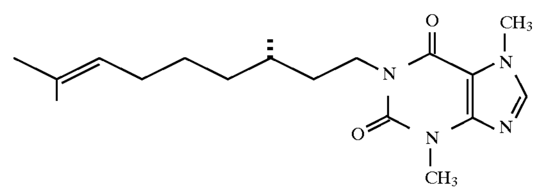 |

| No. | Chemical Name | Chemical Structure |
|---|---|---|
| 1600 | N-(5-hexenyl)glutarimide | 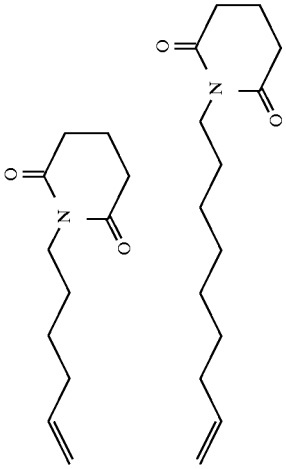 |
| 1604 | N-(8-nonenyl)glutarimide | 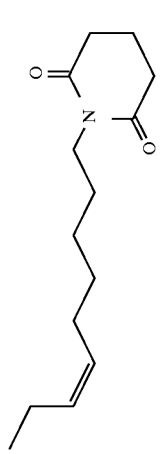 |
| 1607 | N-(6-cis-nonenyl)glutarimide | 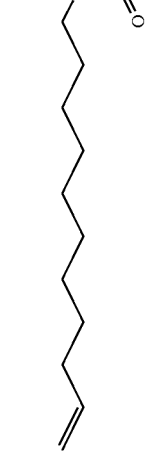 |
| 1610 | N-(10-undecenyl)glutarimide | 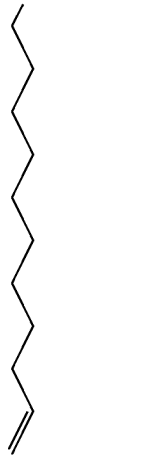 |
| 1615 | N-(10-undecenyl)piperidine | 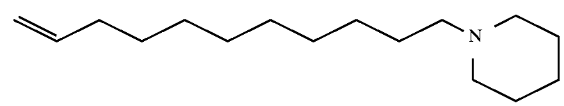 |
| 1616 | N-(10-undecenyl)-2-piperidone | 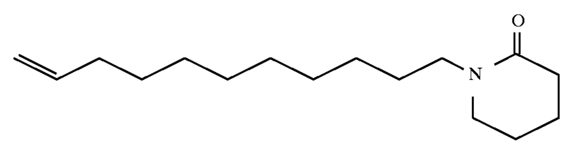 |
| 1624 | N-(10-undecenyl)succinimide | 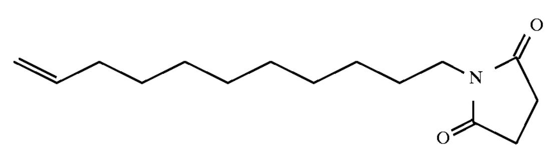 |

-continued

| No. | Chemical Name | Chemical Structure |
|---|---|---|
| 1700 | 2-(5-hexenyl)-1,3-cyclohexanedione | 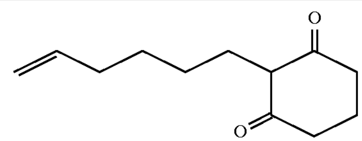 |
| 1701 | 2-(10-undecenyl)-1,3-dimethoxybenzene | 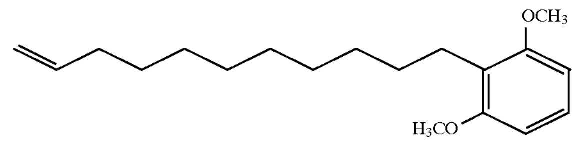 |
| 1702 | 3-(undec-10-enyloxy)cyclohex-2-ene-1-one | 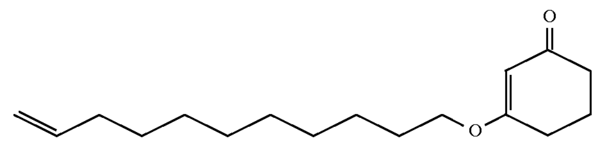 |
| 1704 | N-(10-undecenyl)-N-methylbenzamide | 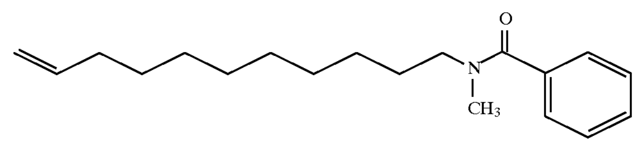 |
| 1800 | 1-methyl-3-(5-hexenyl)uracil | 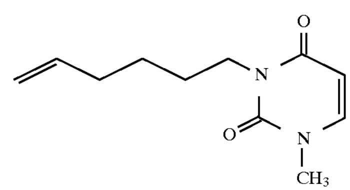 |
| 1812 | 3-(5-hexenyl)-1-methyldihydrouracil | 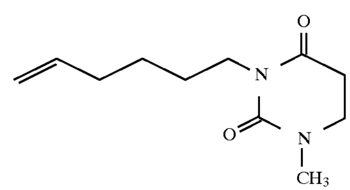 |

-continued

| No. | Chemical Name | Chemical Structure |
|---|---|---|
| 1814 | 3-(6-cis-nonenyl)1-methyluracil | 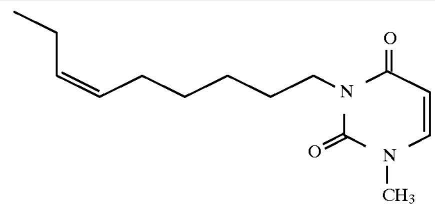 |
| 1817 | 3-(8-nonenyl)1-methyluracil | 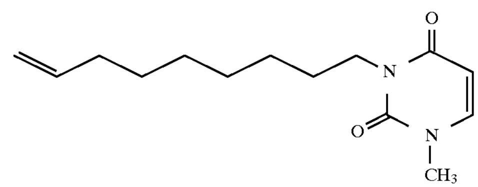 |
| 1819 | 3-(10-undecenyl)-1-methyldihydrouracil | 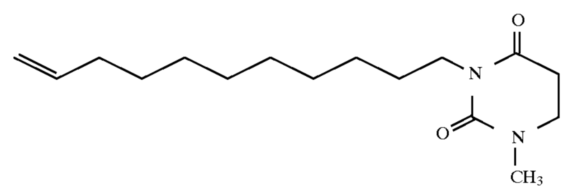 |
| 1823 | 3-(10-undecenyl)1-methyluracil | 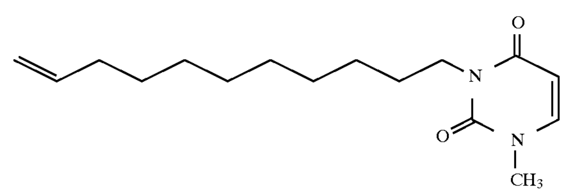 |
| 1905 | 3-(5-hexenyl)-1-methylthymine | 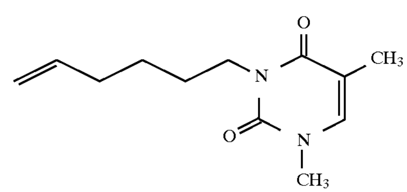 |

-continued

| No. | Chemical Name | Chemical Structure |
|---|---|---|
| 1916 | 3-(6-cis-nonenyl)-1-methylthymine | 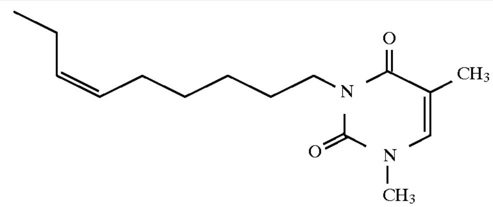 |
| 1917 | 3-(8-nonenyl)-1-methylthymine | 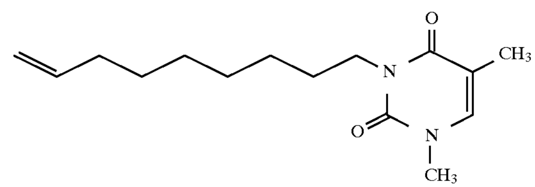 |
| 1931 | 3-(10-undecenyl)-1-methylthymine | 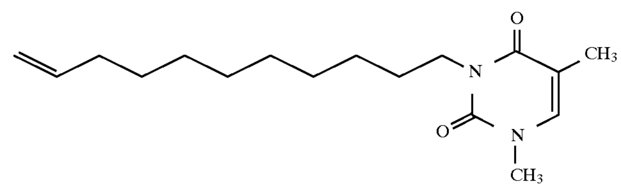 |
| 2501 | 1-(10-undecenyl)-3,7-dimethylxanthine | 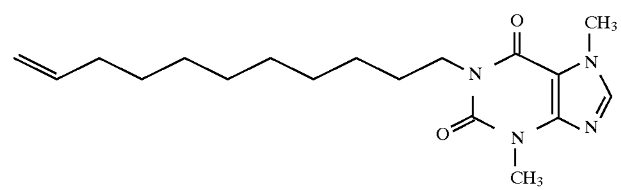 |
| 2503 | 1-(3-butenyl)-3,7-dimethylxanthine | 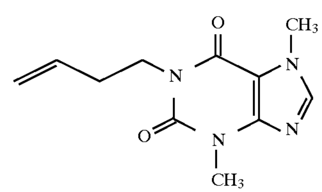 |

| No. | Chemical Name | Chemical Structure |
|---|---|---|
| 2508 | 1-(6-hydroxy-7-octenyl)-3,7-dimethylxanthine | 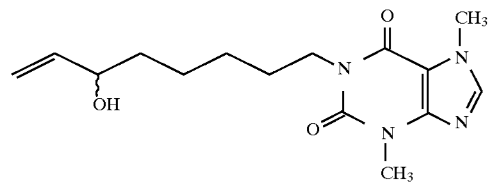 |
| 2512 | 1-(6-trans-nonenyl)-3,7-dimethylxanthine | 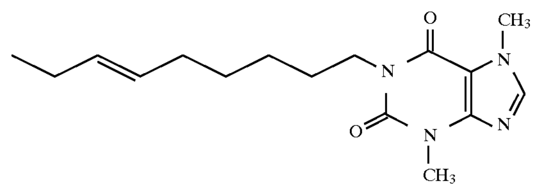 |
| 2516 | 1-(11-dodecenyl)-3,7-dimethylxanthine | 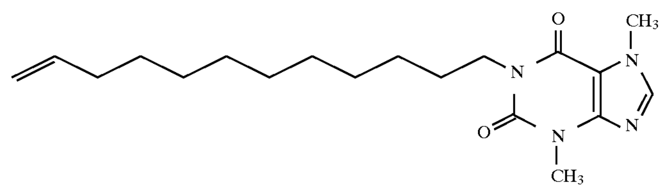 |
| 2536R | 1-(4-(R)-methyl-8-methylnon-7-enyl)-3,7-dimethylxanthine | 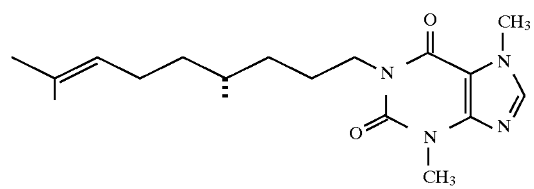 |
| 2536S | 1-(4-(S)-methyl-8-methylnon-7-enyl)-3,7-dimethylxanthine | 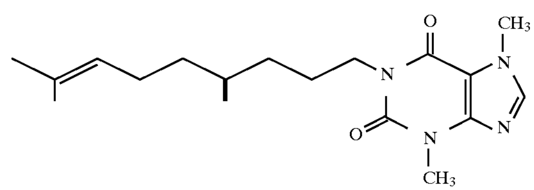 |

-continued

| No. | Chemical Name |
|---|---|
| 2539 | 1-(9-octadecenyl)-3,7-dimethylxanthine |
| 2544 | 1-(farnesyl)-3,7-dimethylxanthine |
| 2545 | 1-(9-geranyl)-3,7-dimethylxanthine |
| 2549 | 1-[6-(9-cis-octadecenoxy)-5-hydroxyhexyl]-3,7-dimethylxanthine |
| 2553 | 1-(6-Butoxy-5-hydroxyhexyl)-3,7-dimethylxanthine |

| No. | Chemical Name | Chemical Structure |
|---|---|---|
| 2555 | 1-(12-tridecenyl)-3,7-dimethylxanthine | 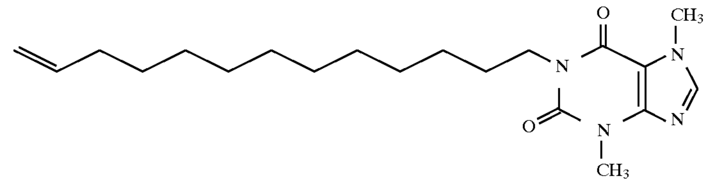 |
| 2560 | 1-(7-cis-decenyl)-3,7-dimethylxanthine | 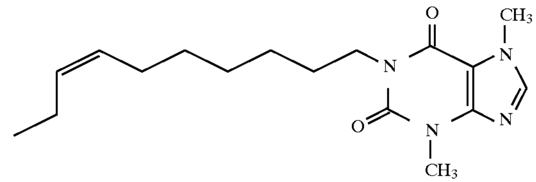 |
| 2568 | 1-(7,8-dihydroxydecyl)-3,7-dimethylxanthine | 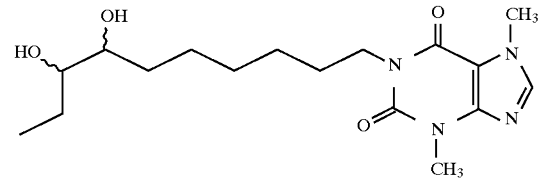 |
| 2569 | 1-(12-Hydroxytridecyl)-3,7-dimethylxanthine | 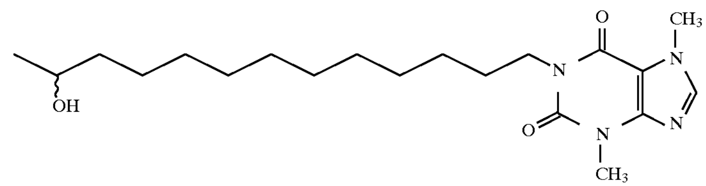 |
| 2577 | 1-(6-allylamino-5-hydroxyhexyl)-3,7-dimethylxanthine | 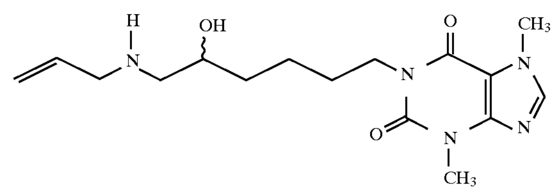 |

| No. | Chemical Name |
|---|---|
| 2578 | 1-(11-Allylamino-10-hydroxyundecyl)-3,7-dimethylxanthine |
| 2589 | 1-(13-tetradecenyl)-3,7-dimethylxanthine |
| 3511 | 1-(16,17-oxidoheptadecyl)-3,7-dimethylxanthine |
| 3521 | 1-(cis,cis,cis-9,12,15-octadecatrienyl)-3,7-dimethylxanthine |
| 3557 | 1-(5-hydroxy-7-carboxy-7-octenyl)-3,7-dimethylxanthine g-lactone |

-continued
| No. | Chemical Name | Chemical Structure |
|---|---|---|
| 3560 | 1-(5-Acetoxyhex-3-enyl)-3,7-dimethylxanthine | 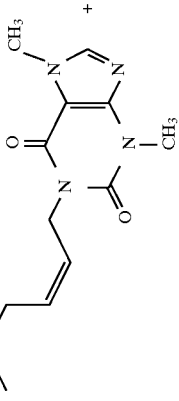 |
| 3566 | 1-(11-Octyloxyundecyl)-3,7-dimethylxanthine | 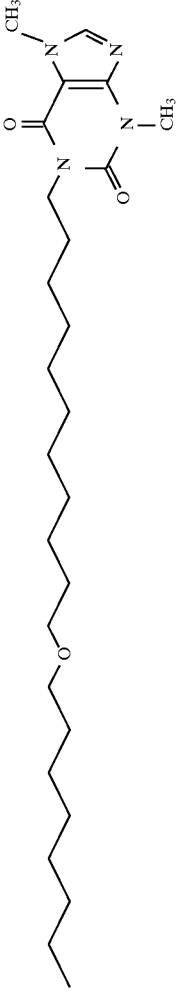 |

Formulation and Dosage

It will be recognized by one of skill in the art that the form and character of the pharmaceutically acceptable carrier or diluent is dictated by the amount of active ingredient with which it is to be combined, the route of administration and other well-known variables. An amino alcohol or chiral secondary alcohol compound or a pharmaceutically acceptable salt or hydrate or solvate thereof is administered to a patient in an amount sufficient to treat or prevent the disease. The route of administration of the illustrated compound (e.g., amino alcohol or chiral primary or secondary alcohol-substituted heterocyclic compound) is not critical but is usually oral or parenteral, preferably oral. The term parenteral, as used herein, includes intravenous, intramuscular, subcutaneous, intranasal, intrarectal, transdermal, opthalmic, intravaginal or intraperitoneal administration. The subcutaneous and intramuscular forms of parenteral administration are generally preferred. The daily parenteral dosage regimen will preferably be from about 0.01 mg/kg to about 25 mg/tkg of total body weight, most preferably from about 0.1 mg/kg to about 4 mg/kg. Preferably, each parenteral dosage unit will contain the active ingredient in an amount of from about 0.1 mg to about 400 mg. The compounds are generally active when given orally and can be formulated as liquids, for example, syrups, suspensions or emulsions, tablets, capsules and lozenges. A liquid formulation will generally consist of a suspension or solution of the compound or pharmaceutically acceptable salt in a suitable liquid carrier(s), for example, ethanol, glycerine, non-aqueous solvent, for example polyethylene glycol, oils, or water with a suspending agent, preservative, flavoring or coloring agent. A composition in the form of a tablet can be prepared using any suitable pharmaceutical carrier(s) routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into a hard gelatin capsule. Alternatively, a dispersion or suspension can be prepared using any suitable pharmaceutical carrier(s), for example, aqueous gums, celluloses, silicates or oils and the dispersion or suspension then filled into a soft gelatin capsule. The daily oral dosage regimen will preferably be from about 0.01 mg/kg to about 40 mg/kg of total body weight. Preferably, each oral dosage unit will contain the active ingredient in an amount of from about 0.1 mg to about 1000 mg.

It will be recognized by one of skill in the art that the optimal quantity and spacing of individual dosages of a compound or a pharmaceutically acceptable salt or hydrate or solvate thereof will be determined by the nature and extent of the condition being treated, the form, route and site of administration, and the particular patient being treated, and that such optimums can be determined by conventional techniques. It will also be appreciated by one of skill in the art that the optimal course of treatment (i.e., the number of doses of a compound or a pharmaceutically acceptable salt or hydrate or solvate thereof given per day and duration of therapy) can be ascertained by those skilled in the art using conventional course of treatment determination tests.

Without further elaboration, it is believed that one skilled in the art can, using the preceding description, utilize the present invention to its fullest extent. Therefore, the following examples are to be construed as merely illustrative and not a limitation of the scope of the present invention in any way.

EXAMPLE 1

This example provides procedures for preparing cell lines used in predictive in vitro assays to obtain results presented in the figures and discussed in subsequent examples. Three cell lines were used: a rat basophilic leukemic cell, RBL-2H3; an IL-3 dependent mouse mast cell (PT-18) and a murine-derived bone marow mast cell (BMMC).

RBL-2H3 cells were grown as monolayers in minimum essential medium with Earle's balanced salt solution containing 16% fetal bovine serum, 2 mM glutamine, 1000 units/ml penicillin and 1000 mg/ml streptomycin.

Another cell line used in these examples is the murine mast cell line, PT-18. These cells are an IL-3-dependent cell line. The PT-18 cells were grown in suspension in RPMI medium containing 10% FBS, 10% WEHI-3 conditioned medium, 25 mM HEPES, 1% non-essential amino acids (GIBCO), 1 mM sodium pyruvate, 50 $\mu$M $\beta$-mercaptoethanal, 2 mM glutamine, 1000 units/ml penicillin and 1000 mg/ml streptomycin.

A third cell culture line used in the in vitro assays described in the examples below is a primary murine bone marrow-derived mast cell. BMMC were prepared according to the following procedures. Bone marrow was extracted from mouse femors with RPMI containing 10% FBS, 2 mM glutamine, 1000 units/ml penicillin and 1000 mg/ml streptomycin. Long-term bone marrow cultures were established in Iscove's medium containing 20% horse serum, hydrocortisone, 1% non-essential amino acids, 1% essential amino acids, and 1 mM sodium pyruvate. Long-term bone marrow cultures were maintained for 5–6 weeks with semi-depopulation feeding. After 5–6 weeks, the remaining non-adherent cells were re-plated in RPMI medium containing 30% FBS, 10% WEHI-conditioned medium, and 100 ng/ml recombinant human stem cell factor (SCF). The resultant cells were characterized for mast cell markers such as toluidine blue staining of granules, surface expression of Fc$\epsilon$RI, and the ability to degranulate and flux calcium after Fc$\epsilon$RI-crosslinking.

EXAMPLE 2

This example illustrates characterization of the bone marrow-derived mast cells prepared in Example 1 above. Characterization in this example was conducted by both toluidine blue staining of granules and flow cytometry analysis to determine expression of Fc$\epsilon$RI.

In the staining method, cytospins of cells were made on microscope slides. Cells were fixed in glutaraldehyde (0.025% glutaraldehyde in 0.1 M Tris and 1% glucose, pH 7.8) for 1 minute at room temperature and then washed 3 times in phosphate-buffered saline (PBS). Cells were stained in toulidine blue (Sigma) (0.0125% wt/vol in PBS) for 15 minutes at room temperature and then rinsed 3 times in PBS. Under microscopic examination, staining with toluidine blue confirmed the presence of multiple granules, characteristic of mast and basophil cells, present in every cell of each BMMC line.

Using flow cytometry, the BMMC examined by staining above were also characterized for specific mast cell markers (i.e., identification of Fc$\epsilon$RI) and compared to the IL-3-dependent mouse mast cell line PT- 18 and the rat basophilic leukemia cell line RBL-2H3.

Figure 1B:
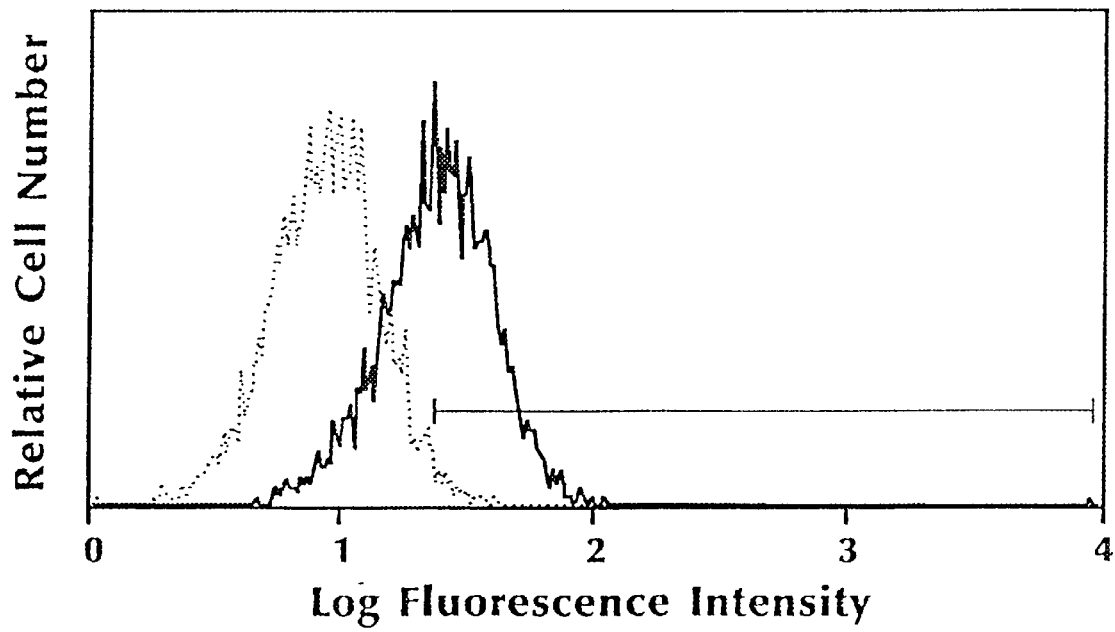

For identification of Fc$\epsilon$RI, approximately $5\times10^5$ cells were incubated in the presence of 1:1000 dilution of anti-TNP IgE for 1 hour at 37° C. in 5% $CO_2$, washed 3 times with PBS, and then incubated with 5 $\mu$g/ml FITC-conjugated anti-IgE on ice. Appropriate controls were prepared using 1:1000 dilution of anti-TNP IgE for 1 hour at 37° C. in 5% $CO_2$ alone, and 5 μg/ml FITC anti-IgE on ice alone. Cells were analyzed on a Coulter Elite flow cytometer. Cells were stimulated with either DNP-HSA or ionomycin and then analyzed on a Coulter Elite flow cytometer. Cell surface expression of the high affinity receptor for IgE, FcεRI, was assessed by flow cytometry using anti-TNP mouse monoclonal IgE and FITC-conjugated anti-IgE to visualize the receptor. Spectra in FIGS. 1A and 1B representing level of expression of FcεRI on the BMMC and PT-18, respectively. As shown, the BMMC are clonal. The entire population of cells expressed FcεRI. The expression of FcεRI on BMMC was comparable to that of PT-18 (FIG. 1B) and RBL-2H3 (not shown).

Finally, in a known method for analysis of calcium flux, cells were sensitized with IgE for 1 hour at 37° C. in 5% $CO_2$, and then loaded with Indo-1 by incubation with its acetoxymethyl ester (available from Molecular Probes) at 1 μM for 45 minutes at 37° C. Both BMMC and PT-18 cells showed an increase in intracellular calcium in response to FcεRI cross-linking.

EXAMPLE 3

This example illustrates phospholipid metabolism in the cell lines prepared and described in Example 1. The assay employs a protocol which emulates mast cell activation in response to allergen. Procedurally, mast cells were quiesced in RPMI medium containing 0.5 % FBS for 18–20 hours. Cells were then sensitized with 1:1000 dilution of ascites of anti-TNP mouse monoclonal IgE for 1 hour at 37° C. in 5% $CO_2$. Anti-trinitrophenol (TNP) mouse monoclonal IgE was obtained from the hybridoma TIB 142 (ATCC).

Unbound IgE was then removed by washing two times in PBS. Cells were treated for 1 hour both in the absence and presence of various concentrations of compounds nos. 1595 and 1604 (see above for chemical names and structures). Cells were then stimulated with 40 ng/ml 2,4-dinitrophenol bound to human serum albumin (DNP-HSA) (available from Sigma) for the indicated times. The reaction was stopped by the addition of 20 volumes chloroform:methanl (2:1 v/v) and lipids were extracted according to the known methods described by Foich et al. and Harris et al. See Folch et al., *J Biol Chem*, vol. 226, 497 (1957) and Harris et al., *Biochim Biophys Acta*, vol. 736, 79 (1983).

Lipids were separated on HPLC and 0.5 minute fractions were collected for subsequent analysis by mass spectroscopy (Example 4). HPLC analysis was performed on a Gilson System 45 with a Waters μ-Porasil silica column (0.45×25 cm). The mobile phase consisted of a gradient of 1–9% water in hexane:isopropanol (3:4 v/v) run at a flow rate of 1 ml/min. Lipids in the column effluent were monitored at 217 nm, the absorption maximum for unsaturated acyl chains. This protocol gives separation of DAG, PA, phosphatidylethanolamine (PE), phosphotidylinositol (PI), phosphatidylserine (PS), phosphatidylcholine (PC), and shingomyelin.

Figure 2:
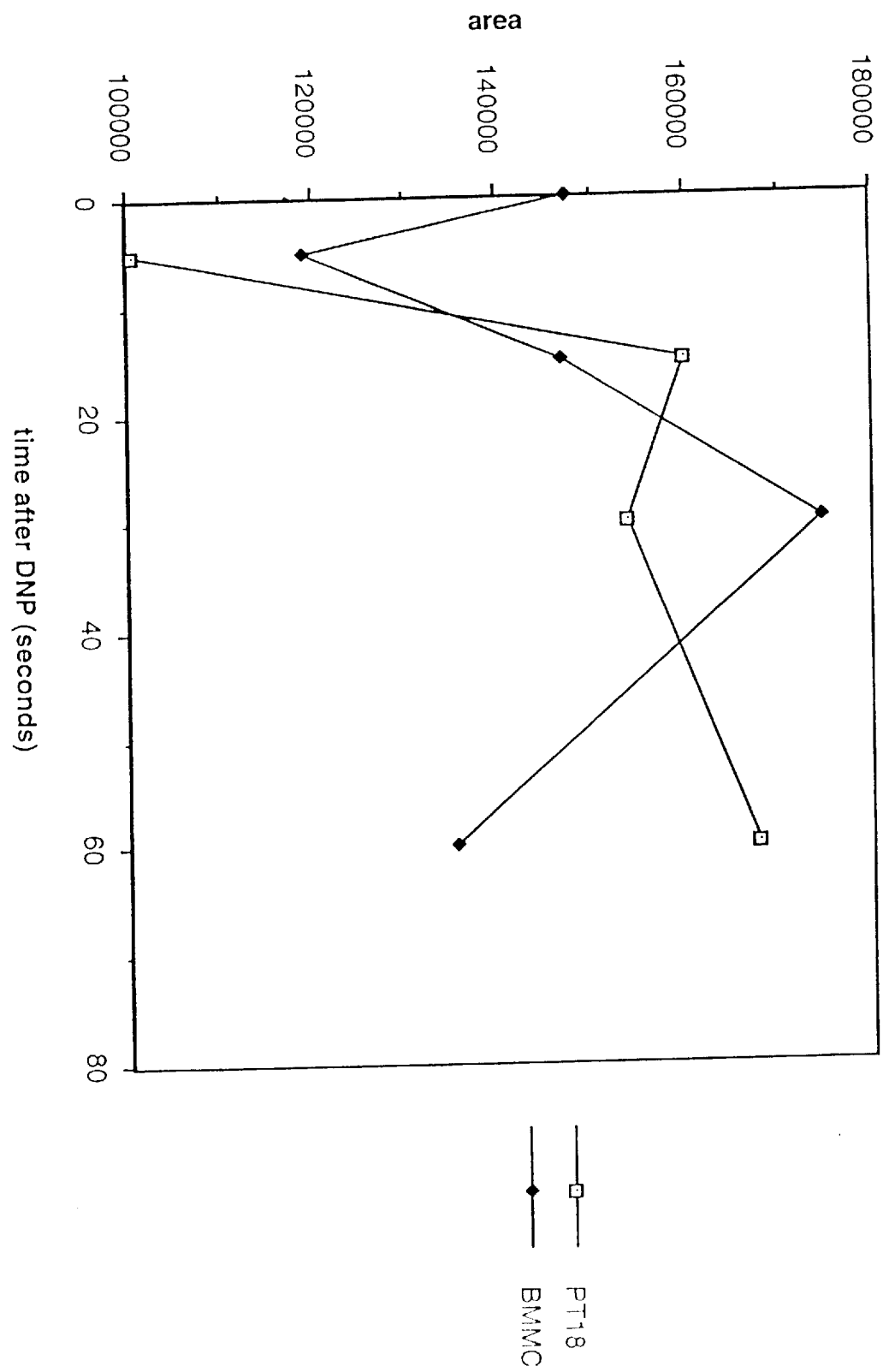
FIG. 2 reports results obtained in an HPLC assay useful in determining PA and DAG generation in response to allergen stimulus.

FIGS. 2 and 3A–3E report results obtained in the foregoing procedure for PT-18 and BMMC cultures in the absence of an inhibitory compound at time periods ranging from 5 to 60 seconds after treatment with DNP. FIG. 2 is a cartesian representation of HPLC peak area versus time (corresponding to the time after treatment with DNP) in each cell line. In these untreated cells, as illustrated in FIG. 2, levels of PA in PT-18 and BMMC increase in response to treatment in this assay, which is predictive of an early phase response to allergen. The production of these phospholipids was observed as early as 5 seconds after stimulation in both cells types. However, PT18 cells appeared to reach a maximum at 15 seconds and then decrease, while BMMC did not reach a maximum until 30 seconds.

Figure 3A:
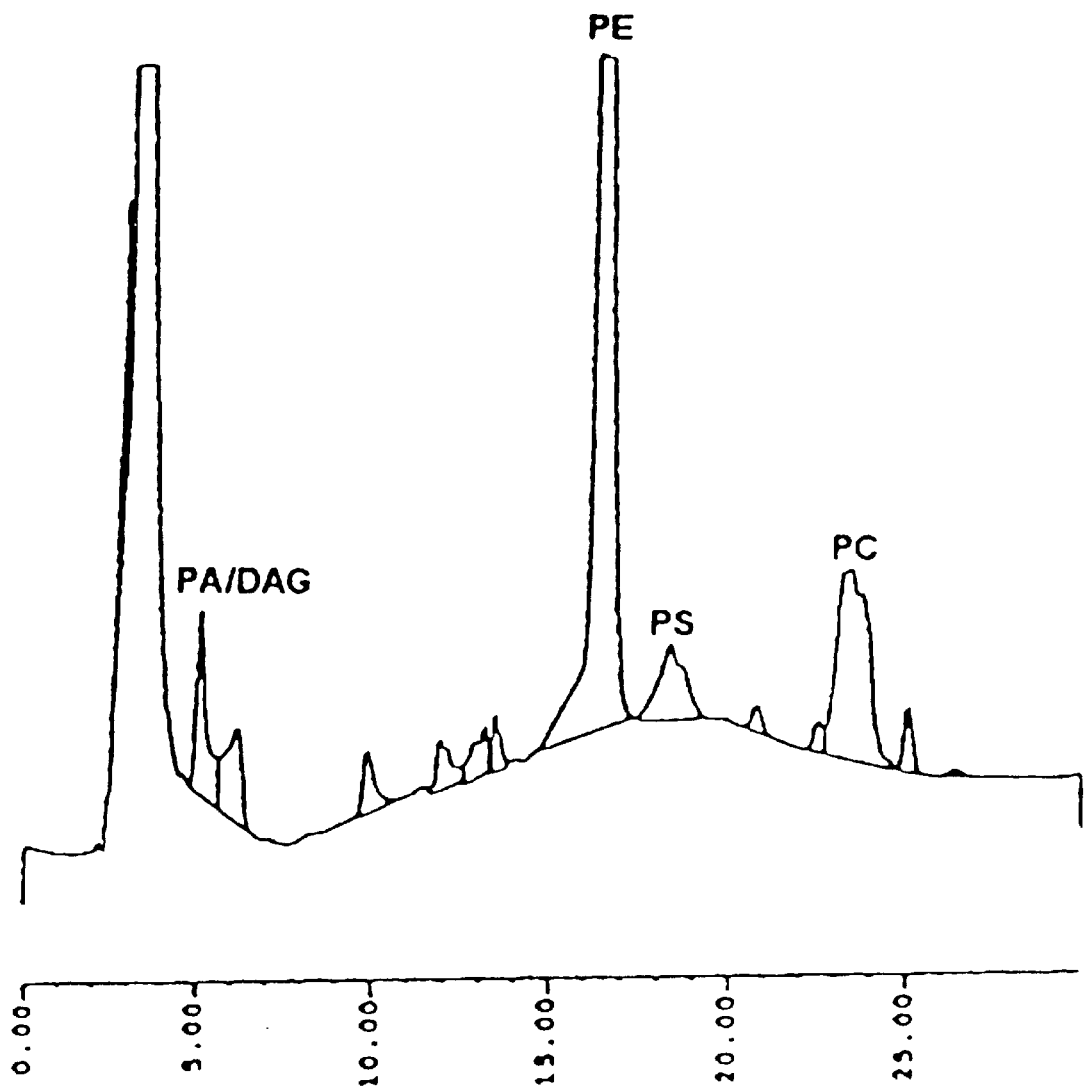
FIGS. 3A–3E report results obtained in an HPLC assay for PT-18 and BMMC cultures in the absence or presence of an inhibitory compound at time periods ranging from 5 to 60 seconds after treatment with DNP-HSA.
Figure 3B:
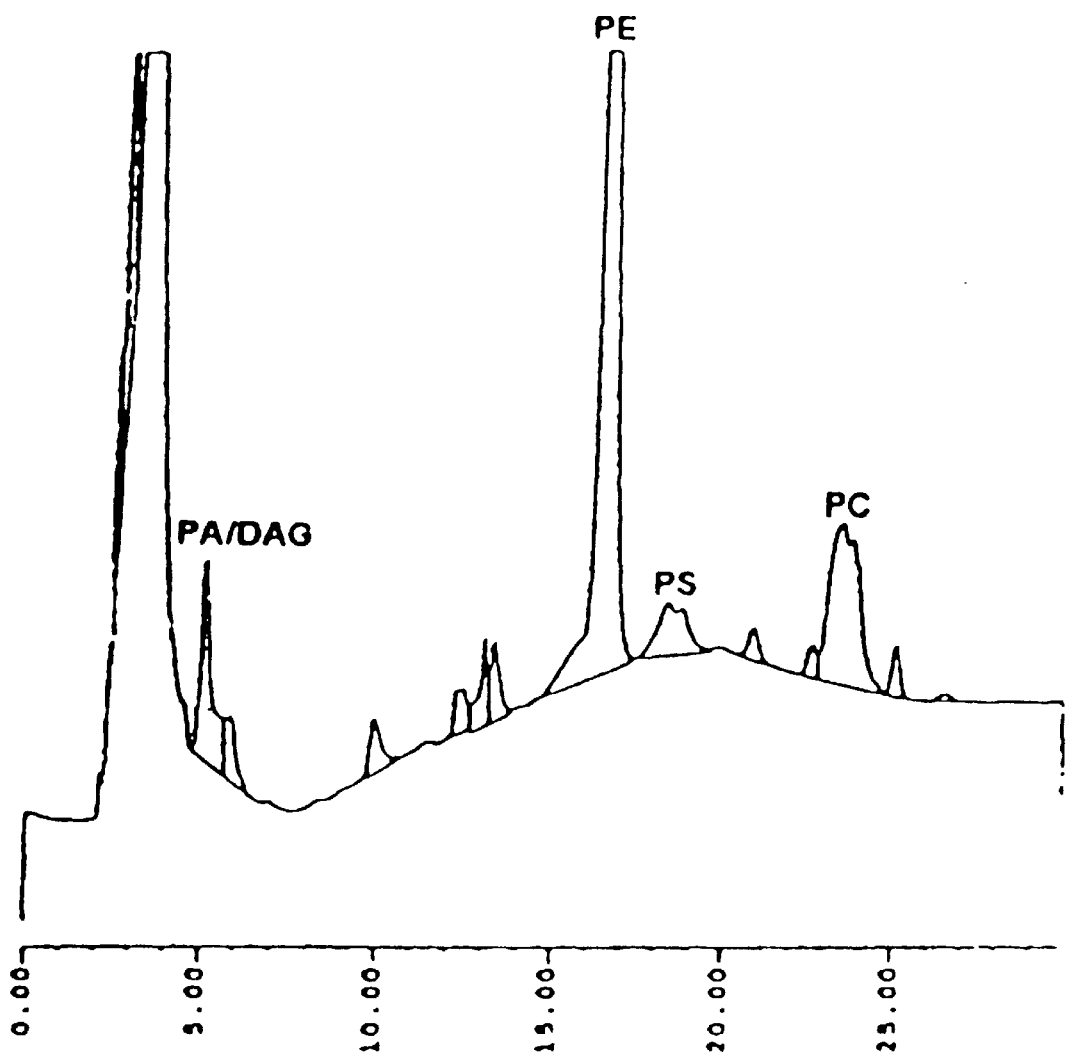
Figure 3C:
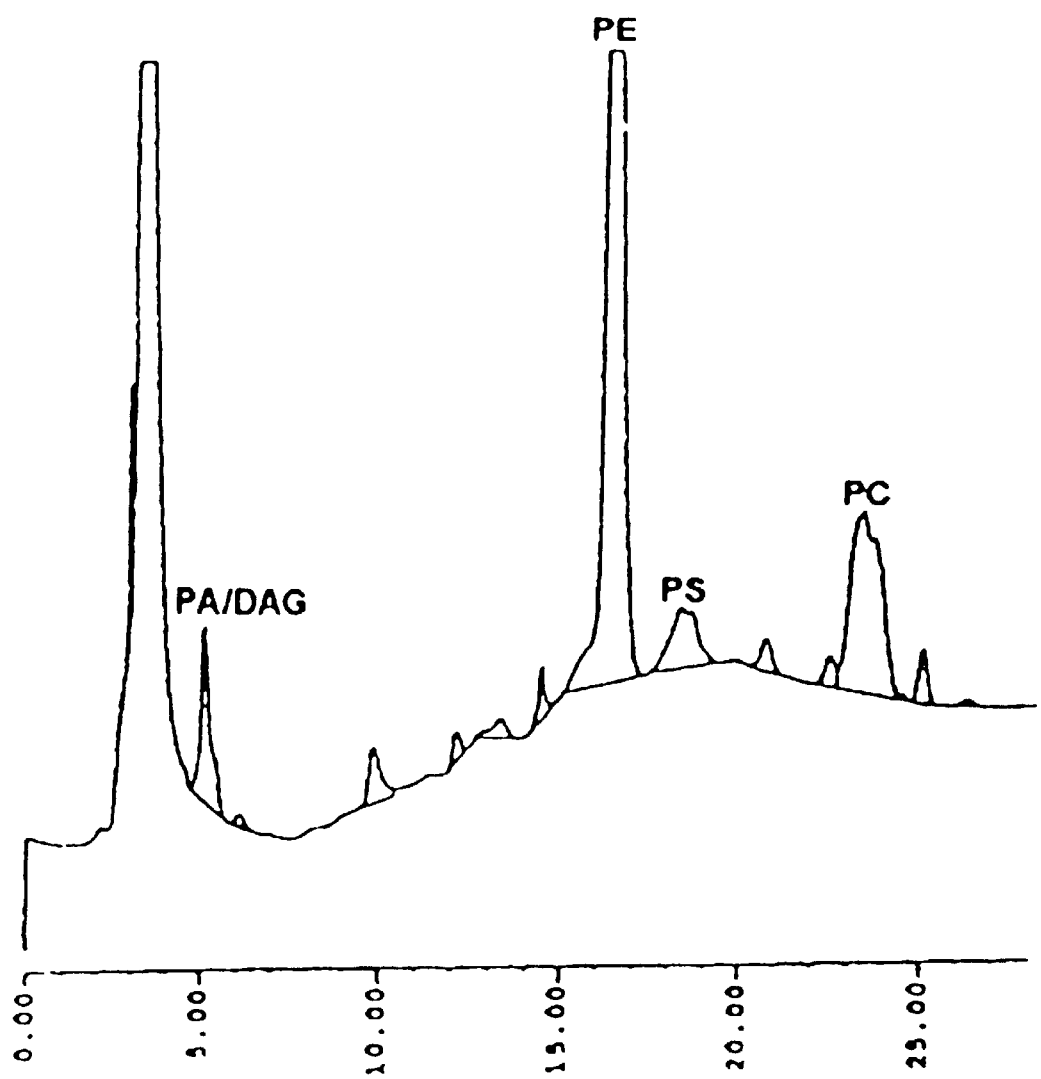
Figure 3D:
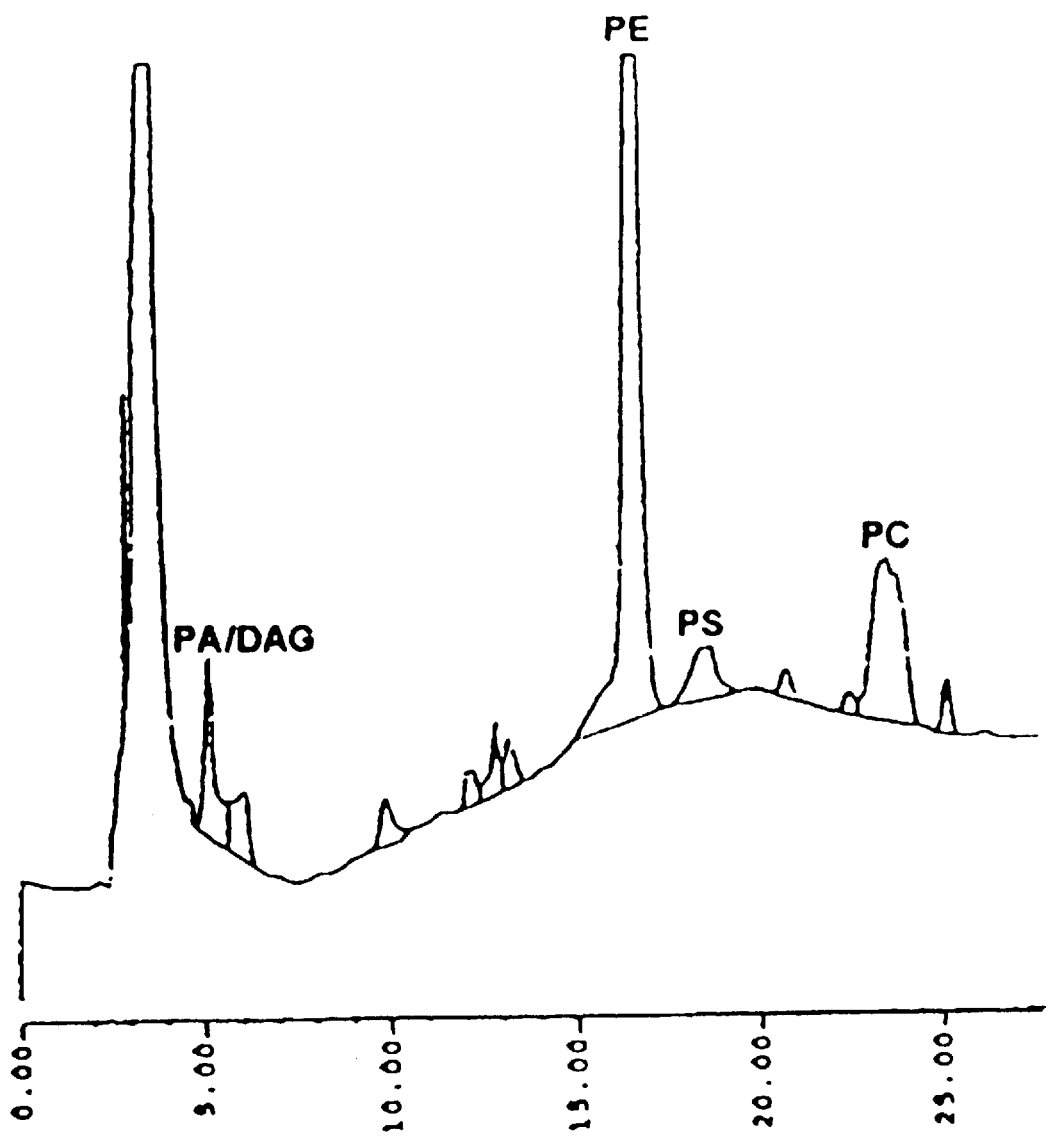
Figure 3E:
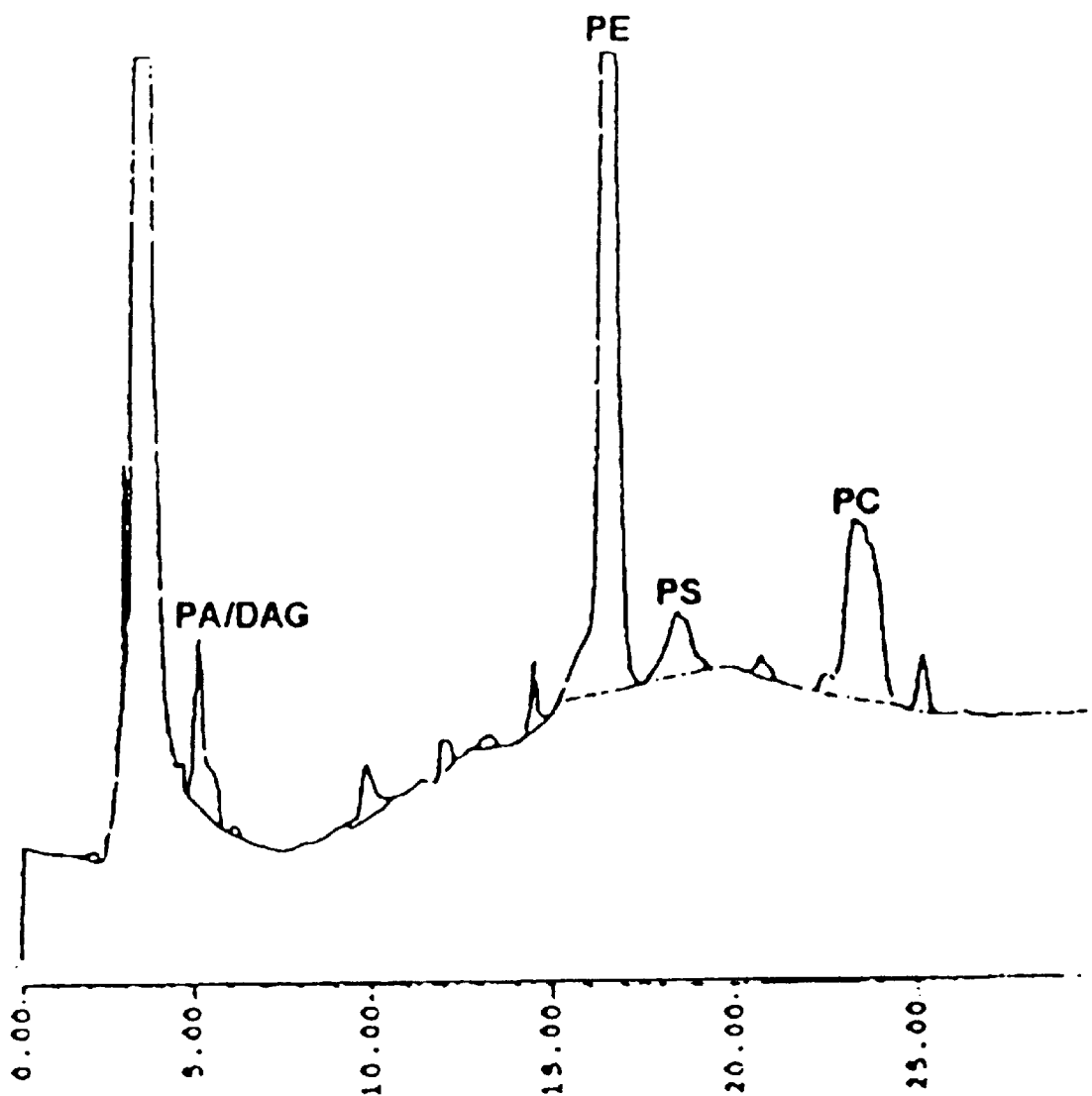

FIGS. 3A–3E compare HPLC spectra obtained in the foregoing assay procedure in both the presence and absence of compounds which inhibit PA and DAG according to the inventive method. FIG. 3A is a spectrum of lipids extracted and separated for cells not treated with compound. FIGS. 3B and 3C correspond to spectra obtained for cultures treated with 10 nM and 50 nM of compound no. 1595, respectively. FIGS. 3D and 3E report HPLC results for cultures treated with 500 nM and 1 μM of inventive compound no. 1604, respectively. Lipid analysis of the untreated cells shown in FIG. 3A accounts for specific and relevant peak at approximately 4.0–6.0 minutes. This peak corresponds to DAG and PA generated in response to allergic stimulus.

In contrast, at 10 nM, compound no. 1595 diminished the appearance of the 4–6 peak (FIG. 3B). At 50 nM, compound no. 1595 eliminated the 4–6 peak from appearing in the HPLC spectrum shown in FIG. 3C. Similarly, at 500 nm and 1 μM, compound no. 1604 diminishes peak 4–6, virtually eliminating the peak at 1 μM, as shown in FIGS. 3C and 3D, respectively. These data illustrate that treatment of PT-18 cells with 500 nM CT1595 or 1 μCT1604 completely inhibited IgE+DNP stimulated PA production. These results confirm inhibition of PA and DAG production in the inventive method by compounds nos. 1595 and 1604, representative of inhibitive compounds.

EXAMPLE 4

This example illustrates identification of PA species generated as a result of allergen response and correspondingly inhibited by compounds employed in the inventive method.

In an assay protocol similar to that discussed in example 3 above, lipids were extracted and-separated on HPLC, and 0.5 minute fractions were collected for analysis by mass spectroscopy. Fast atom bombardment/Mass spectroscopy (FAB/MS) was used in analyzing the relevant PA and DAG species comprising the PA and DAG peaks in the BPLC spectra.

Procedurally, the spectra were acquired using a VG 70 SEQ tandem hybrid instrument of EBqQ geometry (VG Analytical). The instrument was equipped with a standard, unheated VG FAB ion source and a standard saddle-field gun ( IOn Tech Ltd.), producing a beam of xenon atoms at 8 keV and 1mA. The mass spectrometer was adjusted to a resolving power of 1000 and spectra were obtained at 8 kV and at a scan speed of 10 s/decade. Triethanolamine was used as the matrix for negative FAB/MS.

Figure 4B:
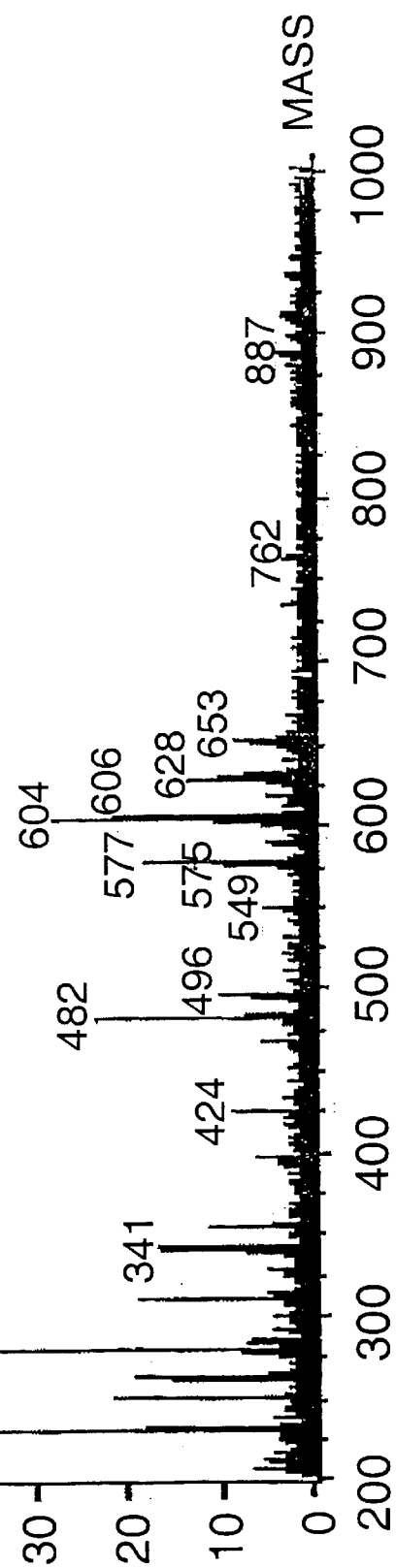
Figure 4C:
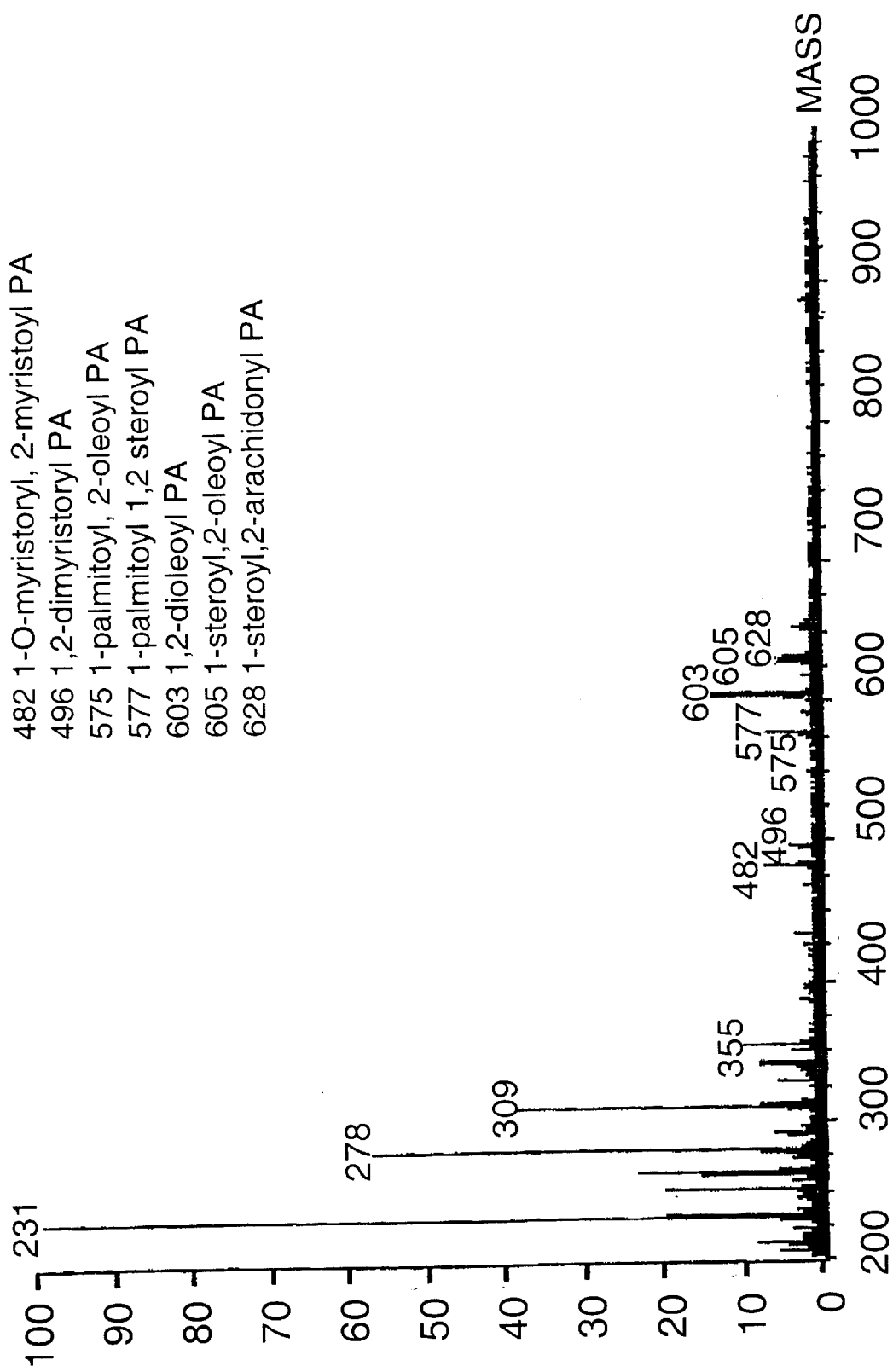
Figure 4D:
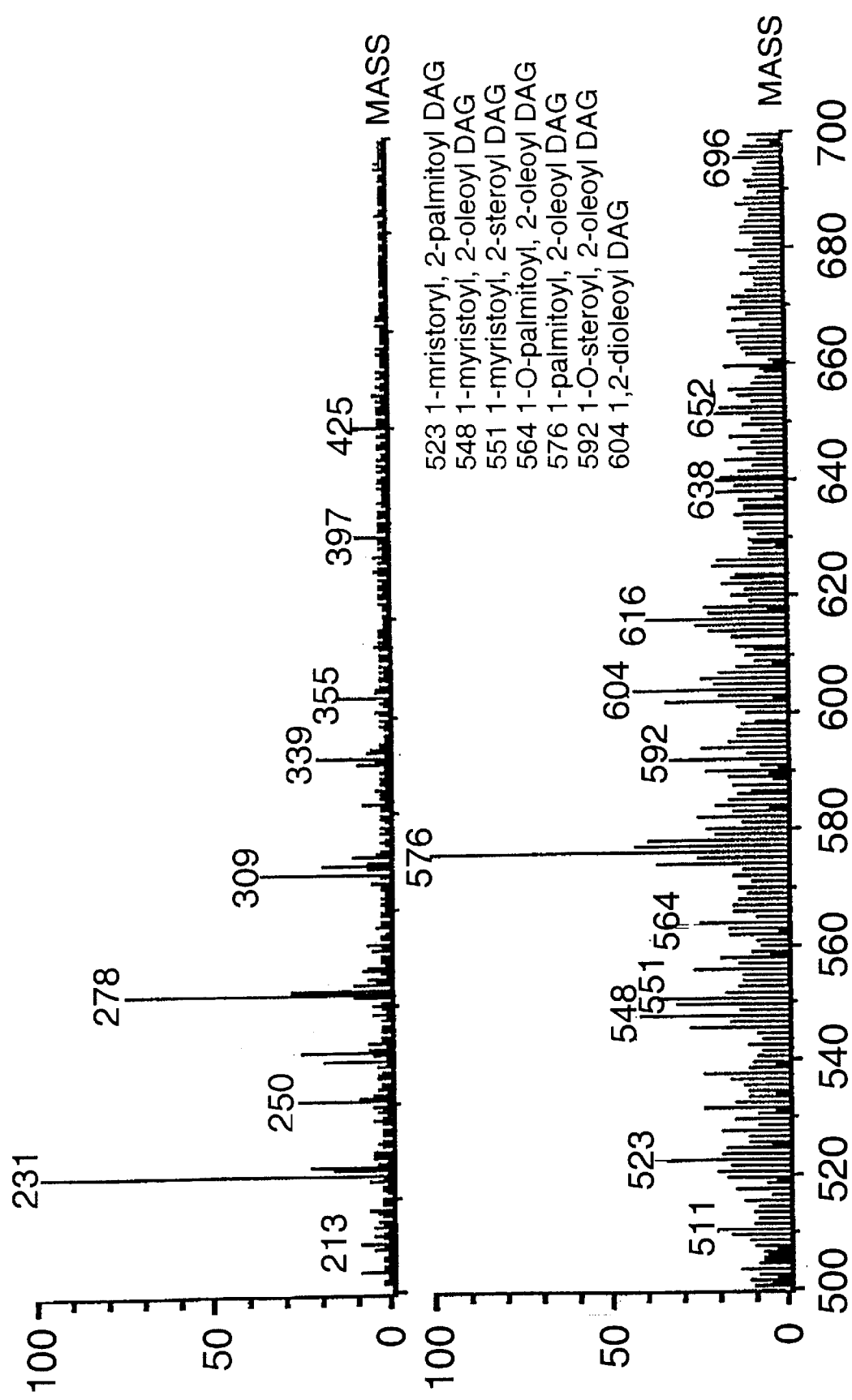
Figure 4E:
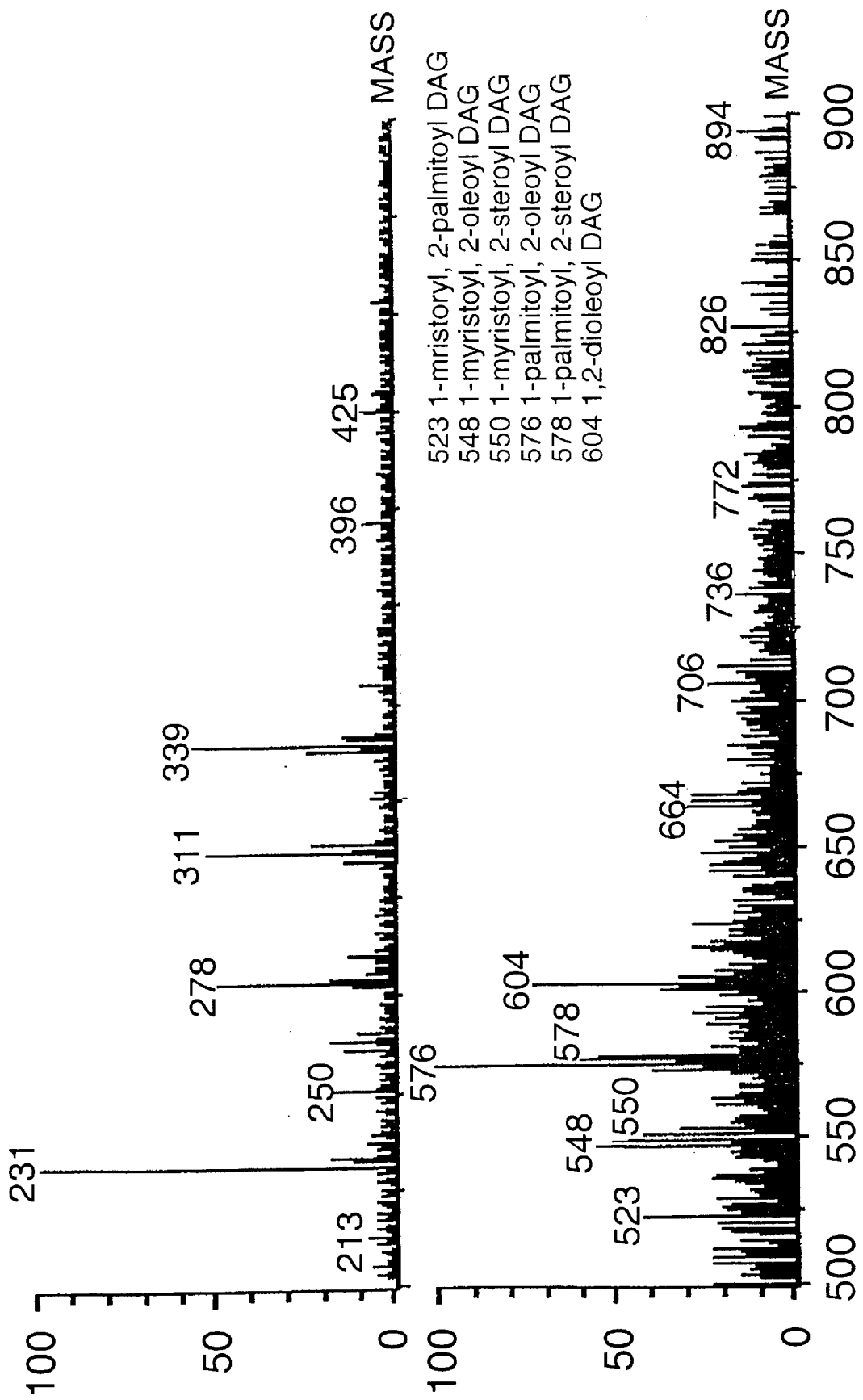

FAB/MS spectra obtained in this assay in the absence of inhibitive compound are shown in FIGS. 4A–4E. FIG. 4A is a spectrum corresponding to an HPLC fraction of PA. FIGS. 4B and 4C are spectra corresponding to TLC fractions of PA. Predominant PA species include 1-O-palmitoyl-2-oleoyl (m/z 660), 1-palmitoyl-2-oleoyl (m/z 673), 1-0-stearoyl-2-oleoyl (m/z 688), 1,2-dioleoyl (m/z 699), and 1-stearoyl-2-oleoyl (m/z, 701) PA.

TLC fractions were obtained in the following protocol, similar to the procedure used for HPLC. Mast cells were quiesced in RPMI medium containing 0.5 % FBS for 18–20 hours. Cells were then sensitized with 1:1000 dilution of ascites of anti-TNP mouse monoclonal IgE for 1 hour at 37° C. in 5% $CO_2$. Unbound IgE was removed by washing two times in PBS. Cells were then stimulation with 40 ng/ml 2,4-dinitrophenol bound to human serum albumin (DNP-HSA) (available from Sigma) for the indicated times. The reaction was stopped by the addition of chloroform and methanol at a ratio of 1:2:0.9 chloroform:methanol:water (v/v). Chloroform and water were added to make a final concentration of 1:1:0.9 chloroform:methanol:water (v/v) and lipids were extracted in the presence of acid according to the method of Bligh/Dyer. Lipids were separated on 10×20 Silica gel G plates (AnalTech). Neutral lipids were separated on TLC using a unidirectional two solvent system. The first solvent system was diethyl ether:benzene:ethanol:acetic acid (40:50:2:0.2 v/v). The second solvent system was diethyl ether:hexane (6:94 v/v). Standards for monoacyl glycerol (MAG), diacylglycerol (DAG), triacylglycerol (TAG), cholesterol, and cholesterol esters (Avanti) were separated by TLC adjacent to the unknown samples. Phospholipids were separated on TLC using chloroform:methanol:20% methyl amine (60:36:10 v/v) as a solvent system. Standards for phophatidic acid (PA), phosphatidylcholine (PC), phosphatidyethanloamine (PE), phosphatidylserine (PS), and phosphatidyl inositol (PI) (Avanti) were separated by TLC adjacent to the unknown samples. For each unkown sample, bands corresponding to the Rf value of the lipid standards were scraped and extracted in the presence of acid using the Bligh/Dyer procedure for analysis by mass spectroscopy. 4D and 4E are also spectra corresponding to TLC fractions of DAG. As shown and labeled in these mass spectra, the PA and DAG species generated 15 seconds after FcεRI crosslinking in PT-18 cells have oleate, stearate, palmitate or myristate in the sn-1 and/or sn-2 positions.

EXAMPLE 5

Because the inventive methods inhibit generation of specific PA and DAG species, and generation of PA and DAG correspond to degranulation and prostaglandin production, this example illustrates the ability of compounds useful in the inventive method to inhibit degranulation. Specifically, this example illustrates degranulation of BMMC, activated by allergen and the effect of compounds nos. 1203, 1604 and 2536 on degranulation. The presence of serotonin in supernatant is a measure of degree of degranulation in response to an allergen stimulus.

In the serotonin assay, adherent cells were seeded at $2 \times 10^5$ cells/well in 24-well plates (CulturPlate-24, Packard). Suspension cells were seeded at $4 \times 10^5$ cells/ml in T25 flasks (Coming) for 18 hours in the presence of 1:1000 dilution of acites of anti-TNP mouse monclonal IgE and 1 $\mu$Ci of [$^3$H]serotonin/ml (5-[1,2-$^3$H]hydroxytryptamine binoxalate) --available from Du Pont-New England Nuclear. Cells were washed twice in isotonic buffer (25 mM disodium PIPES, pH 7.1, 100 mM NaCl, 5 mM KCl, 5 mM glucose, 0.4 mM $MgCl_2$, 1mM $CaCl_2$, and 0.1% BSA), and compounds were added at various concentrations to 250 $\mu$l of isotonic buffer for 1 hour at 37° C. in 5% $CO_2$. Cells were activated with 40 ng/ml DNP-HSA for 45 minutes at 37° C. in 5% $CO_2$. Spontaneous release was measured in cells sensitized with IgE but not activated with DNP-HSA. For adherent cells, the reaction was stopped by removing the supernatant containing the released [$^3$H]serotonin and placing it in a PicoPlate-24, 24 well plate with 1 ml MicroScint-20 liquid scintillation cocktail for counting on the Packard TopCount. [$^3$H] serotonin incorporated into the cells was determined by lysing cells in 1% Triton X-100 in phosphate-buffered saline and then adding MicroScint-20 directly to the CulturPlate-24 for counting on the Packard TopCount. For suspension cells, the reaction was stopped by centrifugation of the cells and removal of the supernatant. The cell pellet was lysed in 1 % Triton X-100 to measure [$^3$H]serotonin incorporation. Assays were done in duplicate. Specific release was defined as that portion of the total radioactivity recovered from the supernatant, after subtraction of spontaneous release. The percentage inhibition was then calculated from these values.

Figure 5:
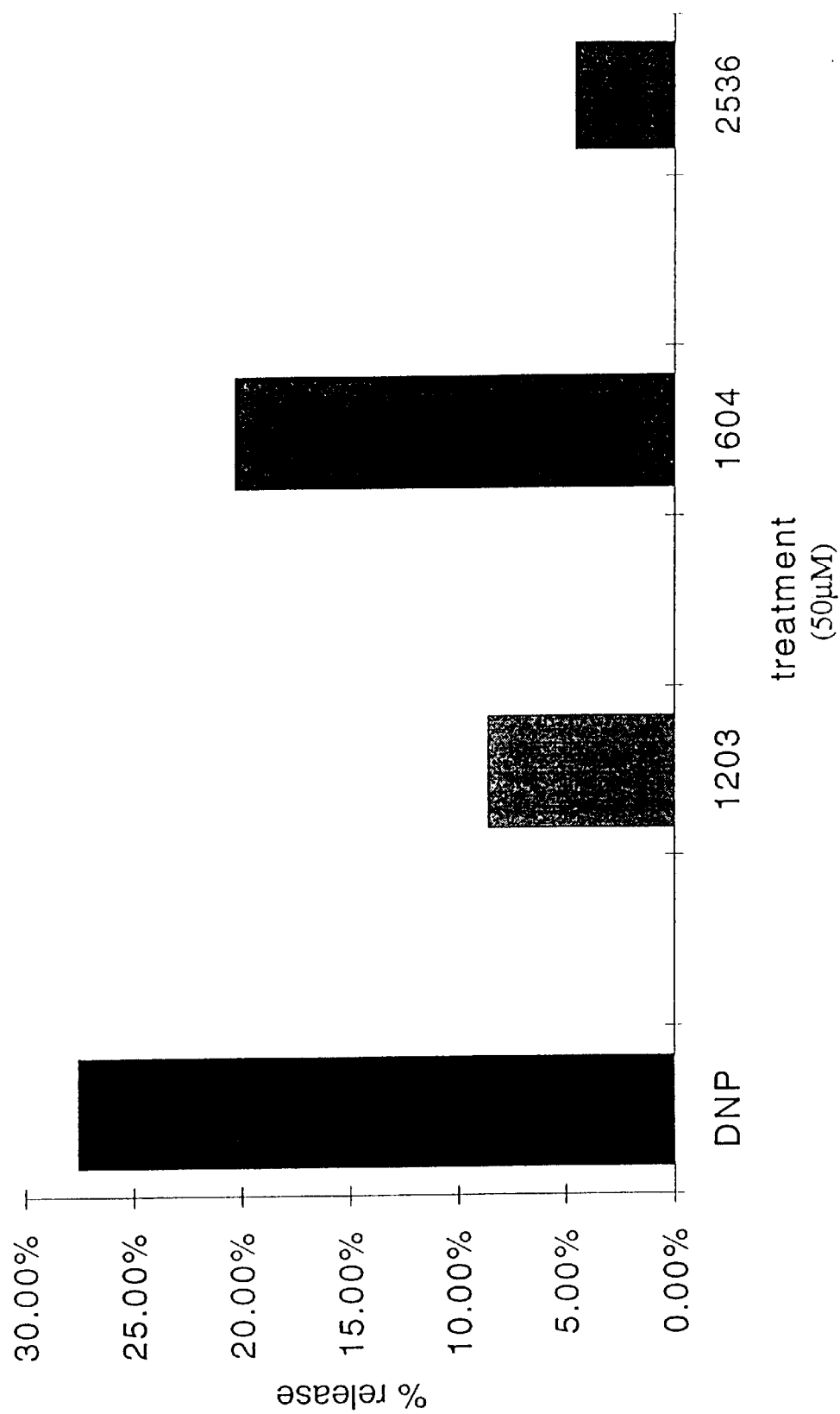
FIG. 5 illustrates results for BMMC in a serotonin-release assay used to confirm that the inventive method inhibits degranulation.

FIG. 5 illustrates results for BMMC in the previously-described serotonin-release assay. Shown are % release of serotonin for a control and cell cultures treated with compounds nos. 1203, 1604 and 2536. As shown in FIG. 5, the untreated control exhibits BMMC degranulation at a relative % serotonin release of about 27.5% 45 minutes after stimulation. This was comparable to the percent [$^3$H]serotonin release normally seen in RBL-2H3 cells. Pretreatment of BMMC with 1203, 1604, and 2536, resulted in a 26% to 83% inhibition of [$^3$H]-serotonin release at a concentration of 50 $\mu$M.

EXAMPLE 6

This example illustrates how representative compounds of the inventive method inhibit degranulation as compared with a corticosteroid, beclomethasone.

Figure 6:
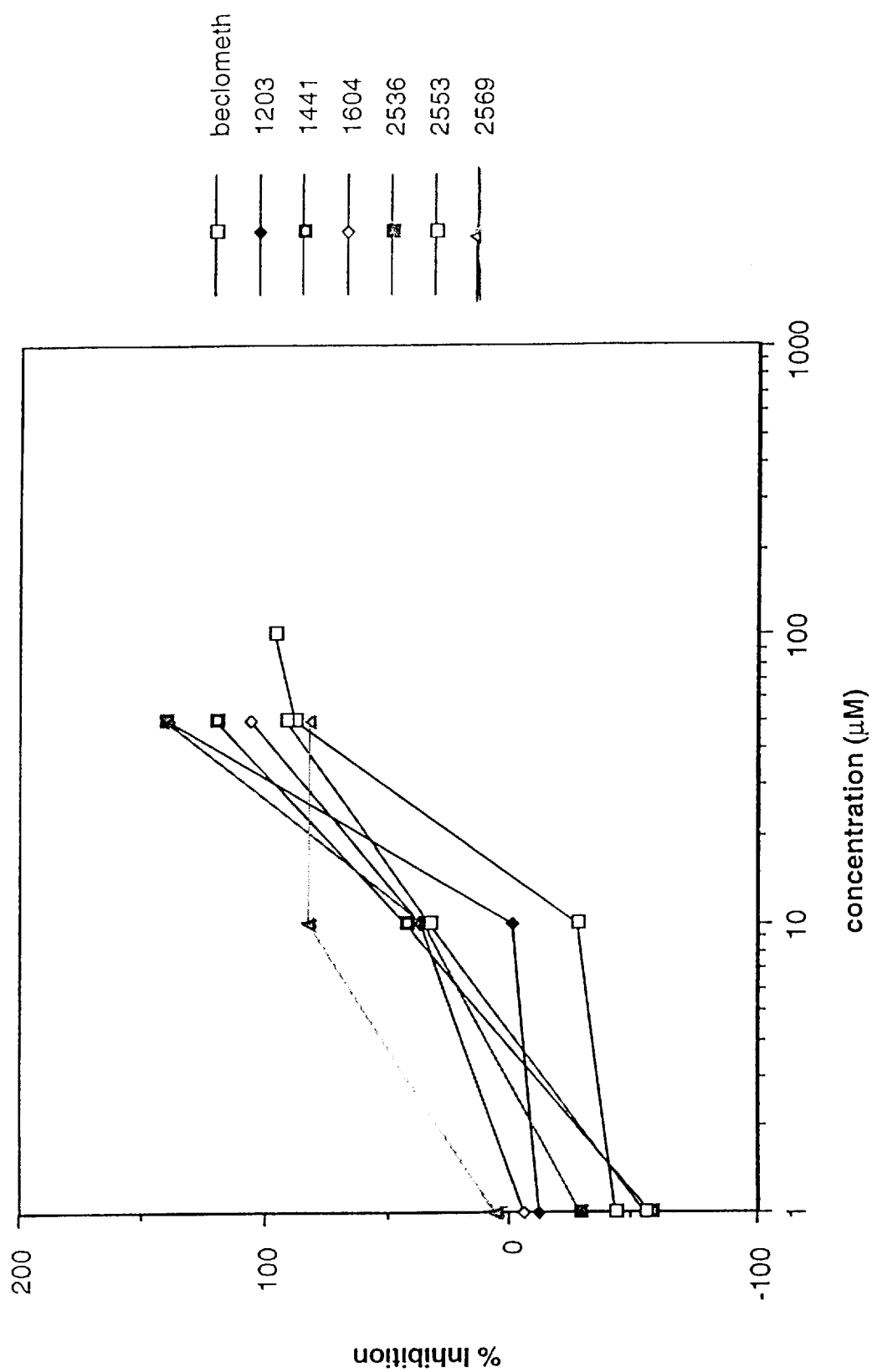
FIG. 6 reports results obtained in a serotonin assay used to obtain data presented in FIG. 5, with the exception that the assay was performed with the RBL-2H3 leukemic basophil cell system.

In an assay similar to the protocol utilized for the foregoing BMMC analysis (Example 5), experiments were conducted using compounds nos. 1203, 1441, 1604, 2536, 2553 and 2569 and the comparative corticosteroid in an RBL-2H3 cell system. The results from this assay are reported in FIG. 6. The most active of the compounds, representative of compounds of the inventive method, inhibited degranulation in a dose-response manner, with $IC_{50}$s of ranging from approximately 10–15 FLM. In comparison, the corticosteroid, beclomethasone, had an $IC_{50}$ of ~40 $\mu$M in this assay. These results confirm that the compounds tested inhibit degranulation of the RBL-2H3 leukemic basophils.

EXAMPLE 7

This example illustrates that the inventive method inhibits degranulation by interfering with PA and DAG generation and not by inhibition of protein tryrosine kinase (PTK). Other, known PTK inhibitors, such as for example, genestein and tyrophostin 47 inhibit mast cell degranulation, but through inhibiting PTK.

In this assay, RBL-2H3 cells were sensitized with 1:1000 dilution of ascites of anti-TNP mouse monoclonal IgE for 1 hour at 37° C. in 5% $CO_2$, followed by treatment for 1 hour with various concentrations of inhibitive compound no. 1604. Cells were then stimulated with 40 ng/ml DNP-HSA for the indicated times. Cells were solubilized in lysis buffer containing 1% Nonidet P-40, 50 mM Tris-HCl, pH 8.0, 150 mM NaCl, 2 mM EDTA, 10 $\mu$g/ml aprotinin, 10 $\mu$g/ml leupeptin, and 1 mM sodium orthovanadate. Insoluble debris was removed by centrifugation. Anti-phosphotyrosine (APT) immunoblots were preformed using conventional techniques.

Figure 7:
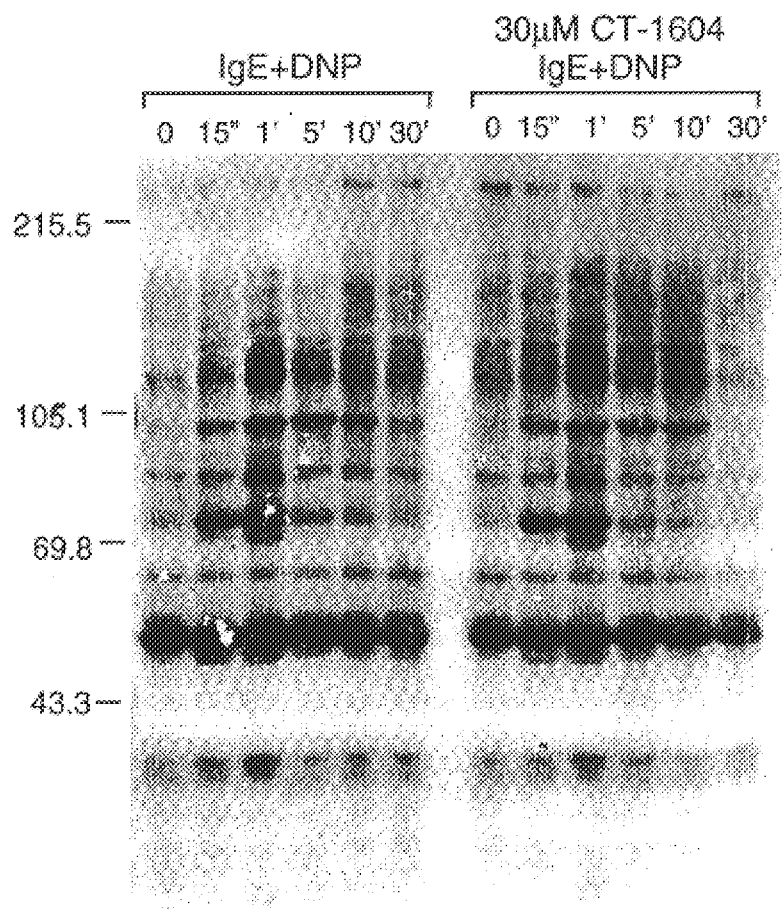
FIG. 7 illustrates that stimulation through FcεRI induced the phosphorylation of several distinct proteins on tyrosine residues in both the absence and presence of inhibitive compound no. 1604.

A representative blot is shown in FIG. 7. FIG. 7 illustrates that whole cells lysates reveals that stimulation through FcεRI induced the phosphorylation of several distinct proteins on tyrosine residues in both the absence and presence of inhibitive compound no. 1604. A time course of activation revealed that compound no. 1604, representative of the inhibitive compounds, has no effect on tyrosine kinase activity and protein tyrosine phosphorylation. Specifically, compound no. 1604 had no apparent effect on the kinetics of protein tyrosine phosphorylation at a concentration of 30 $\mu$M, which is two times its $IC_{50}$. In addition, inhibitive compound 1604 had no effect on the amount of tyrosine phosphorylation observed.

EXAMPLE 8

This example investigates an ability of the inhibitive compounds of the inventive method to inhibit production of $PGE_2$. Procedurally, cells were seeded at $1 \times 10^5$ cells/well in 24-well plates. After 4–6 hours of culturing the medium was replaced with medium containing 0.5% fetal bovine serum for 18 hours. Cells were sensitized with 1:1000 dilution of ascites of anti-TNP mouse monoclonal IgE for 1 hour at 37° C. in 5% $CO_2$, followed by treatment for 1 hour with various concentrations of inhibitive compounds nos. 1203, 1441 or 1604. Cells were then stimulated with 40 ng/ml DNP-HSA for 18–20 hours. The reaction was stopped by removing the supernatant containing the released $PGE_2$ and removing any detached cells by centrifugation. $PGE_2$ production was determined by using the Advanced Magnetics Inc. Prostaglandin E2 EIA Assay kit.

Figure 8:
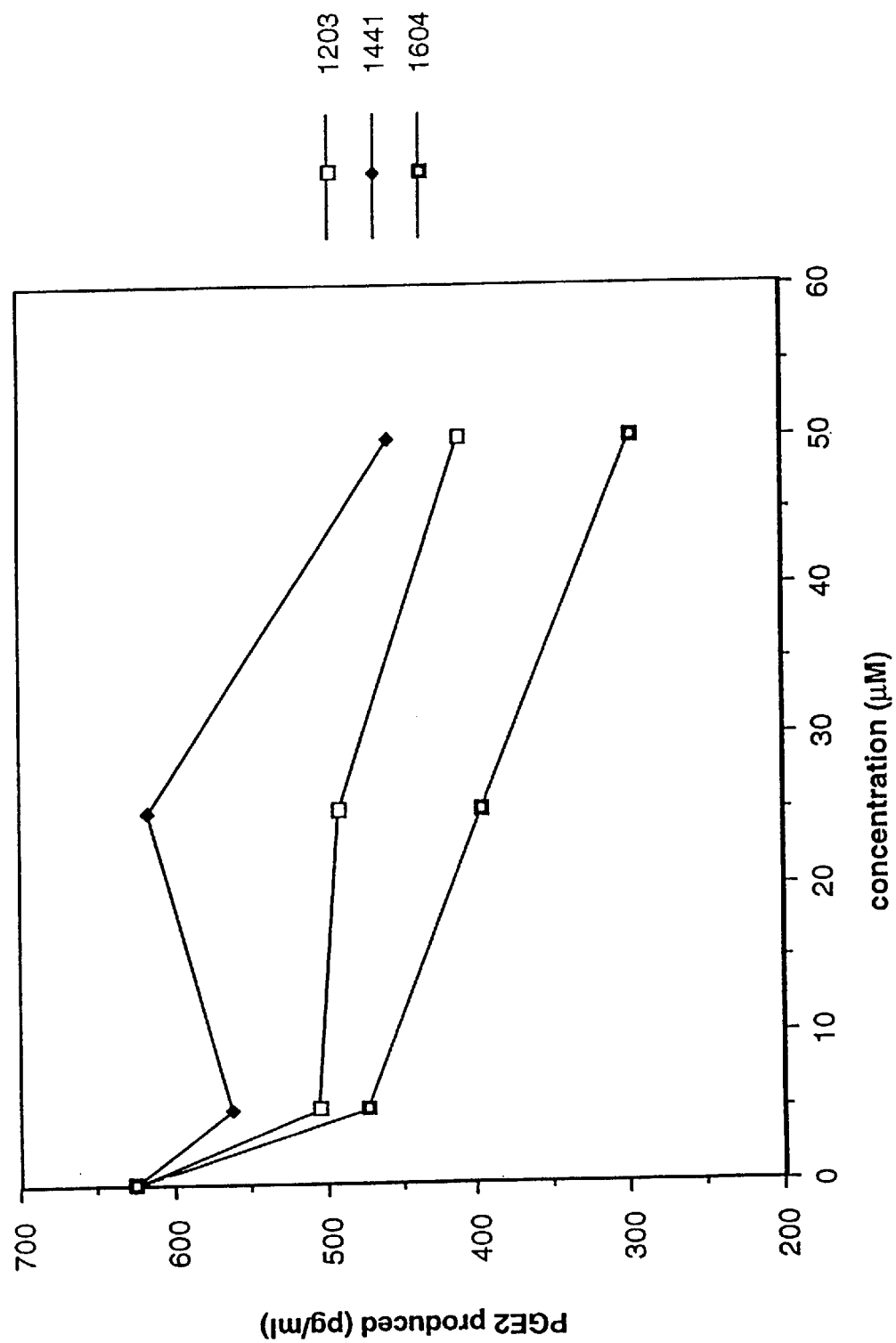
FIG. 8 illustrates that the inventive method by inhibiting PA and DAG production, interferes with FcεRI-mediated production of PGE2.

Results are reported in FIG. 8 for the compounds tested. The results show that the compounds tested, representative of compounds of the inventive method, inhibit FcεRI-mediated production of PGE2.

EXAMPLE 9

This example illustrates how representative compounds of the inventive method cause approximately a two-fold increase in PKC activity in the membrane of RBL-2H3 cells. This activation of PKC activity occurs in the presence or absence of activation through FcεRI.

This assay employs a protocol which emulates mast cell activation in response to allergen. Procedurally, RBL-2H3 cells were sensitized with a 1: 1000 dilution of ascites of anti-TNP IgE for 1 hour at 37° C. in 5% $CO_2$. Unbound IgE was removed by washing two times in PBS. Cells were treated for 1 hour both in the absence and presence of 50 μM compound no. 1604 (see above for chemical names and structure). Cells were then stimulated with 40 ng/ml DNP-HSA for the indicated times. The reaction was stopped by washing two times with ice cold PBS and then adding 1 ml ice cold Buffer A (20 mM Hepes pH 7.5, 10 mM EGTA pH 7.5,2 mM EDTA pH 7.5, and 300 mM DTT). Cells were homogenized by douncing 20 times. Samples were then centrifuged for 20 minutes at 4° C. at 100,000g. After centrifugation the supernatent, which contains the cytoplasmic PKC, is removed and saved. The pellet, which contain the membrane bound PKC, is solubilized in Buffer A plus 0.1% Triton X-100 by passing through a 22 gauge syringe 5–10 times and then a 25 gauge syringe 5–10 times. The solubilized membrane is then centrifuged for 20 minutes at 40° C. at 100,000g. After centrifugation, the supernatent, which contains the membrane-associated PKC, is removed and saved. PKC activity in cytoplasmic and membrane fractions was measured using the specific peptide substrate KRTLRR. PKC activity was assayed in 50 μl reaction mix containing 20 mM Hepes pH 7.5, 10 mM $MgCl_2$, 0.6 mM EDTA, 5.6 mM dityiothreitol, 200 mM KRTLRR, 50 μM [$^{32}$P]ATP (1000–3000 cpm/pmol). After a 10 minute reaction time, the reaction was stopped by spotting 40 μl of the reaction mixture on phosphocellulose paper (Whatman P-81, Fischer Scientific). The papers were extensively washed in 0.1% phophoric acid and the radioactivity counted. Background activity was determined in samples in which KRTLRR was omitted and theses values were subtracted from assay values. Protein analysis of cytosolic and membrane preparations were performed using the Pierce Coomassie Plus Protein Assay Reagent in 96-well moicrotiter plates. Results are expressed as picomoles of phosphate per mg of protein per minute and are the mean of triplicate assays minus blanks for each time point.

Figure 9:
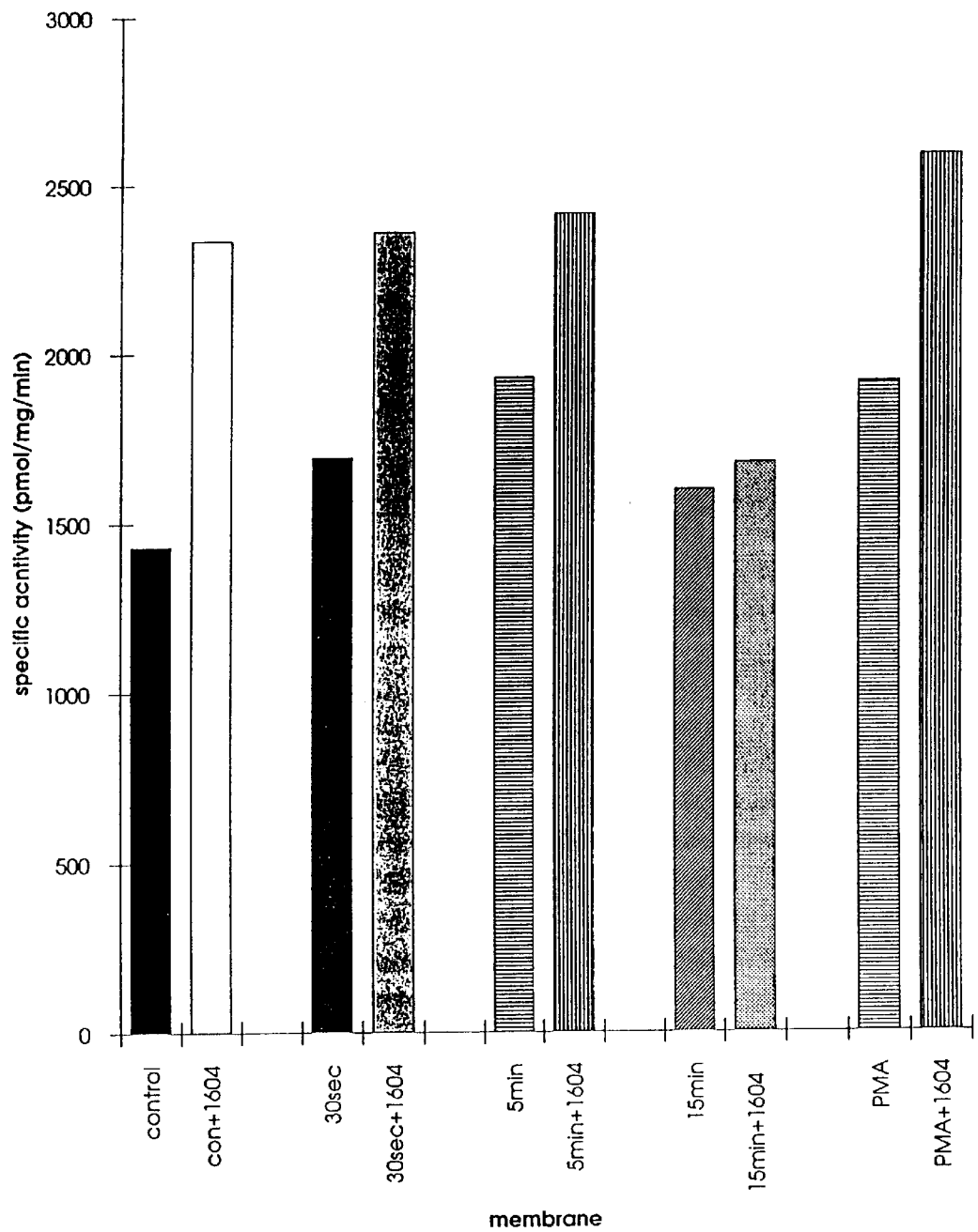
FIG. 9 illustrates results for PKC Assays in the procedure described in Example 9.

FIG. 9 illustrates results for PKC assays in the previously described procedure. Shown are the specific activity (pmol/mg/min) for unactivated (control) cells and cells activated with IgE+DNP for 30 seconds, 5 minutes, and 15 minutes. Cells treated with 50 ng/ml PMA are shown as a positive control for PKC activation. The experiment was done both in the presence and absence of compound no. 1604. As shown in FIG. 9, activated and unactivated (control) cells show approximately a 2-fold increase in PKC activity in the membrane of RBL-2H3 cells in the presence of compound no. 1604.

What is claimed is:

1. A method for treating allergy or allergic disorders, comprising the step of administering an effective amount of a compound to inhibit intracellular generation of phosphatidic acid and diacylglycerol, the intracellular generation resulting from allergen presentation or mast cell or basophil activation, the compound or pharmaceutical composition thereof selected from:

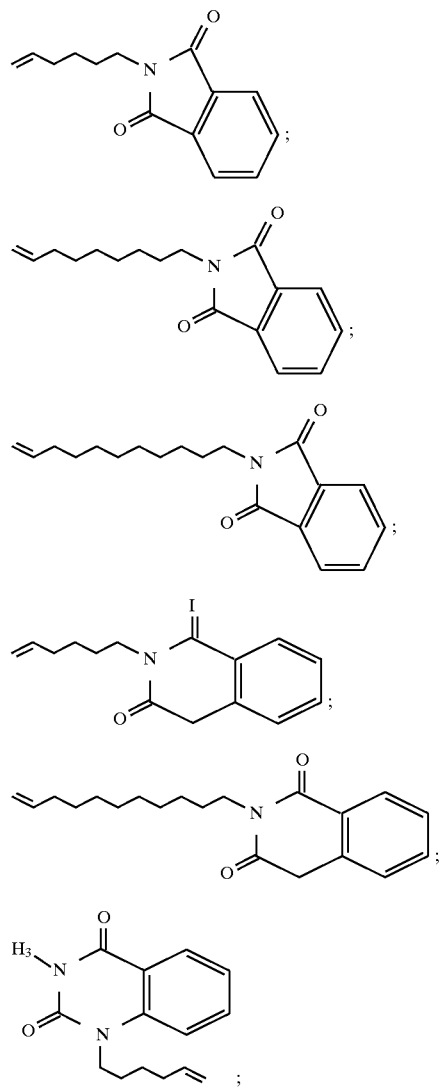

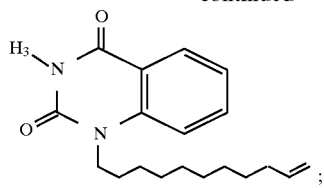
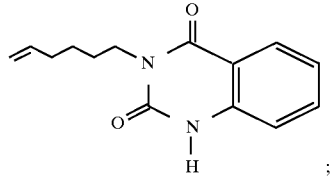
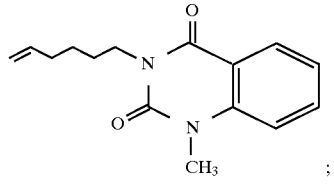
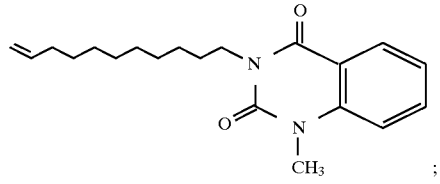
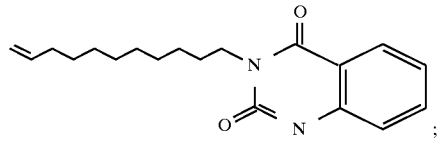
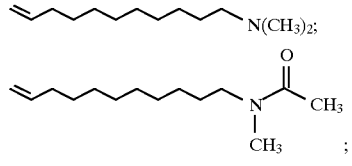
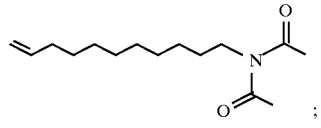
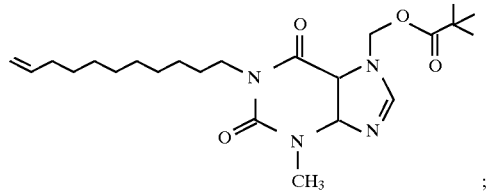
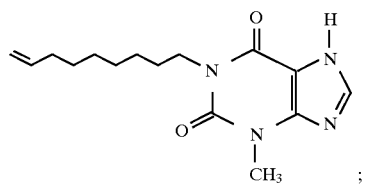
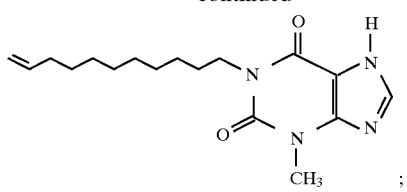
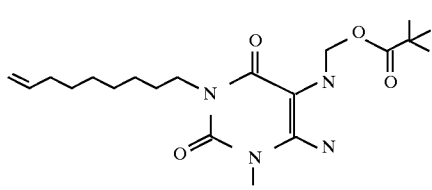
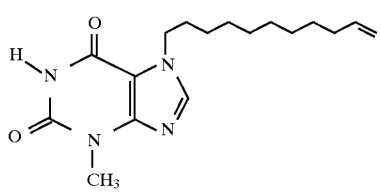
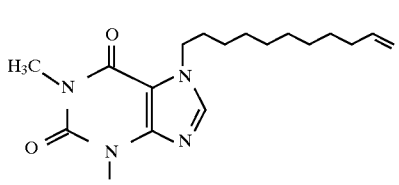
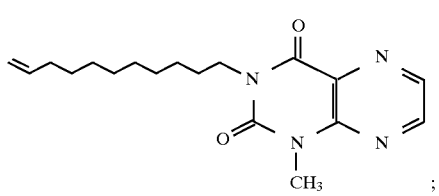
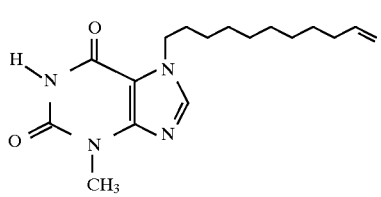
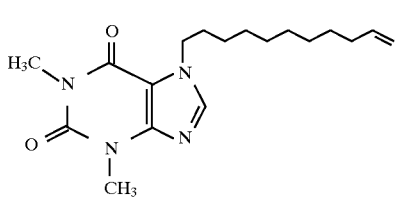
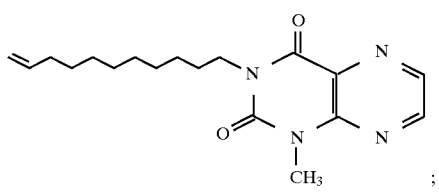

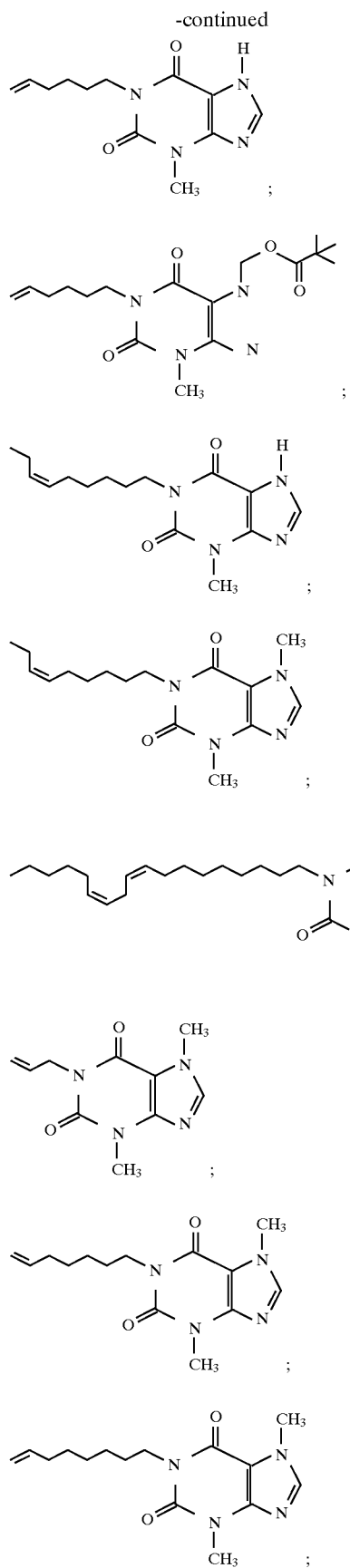
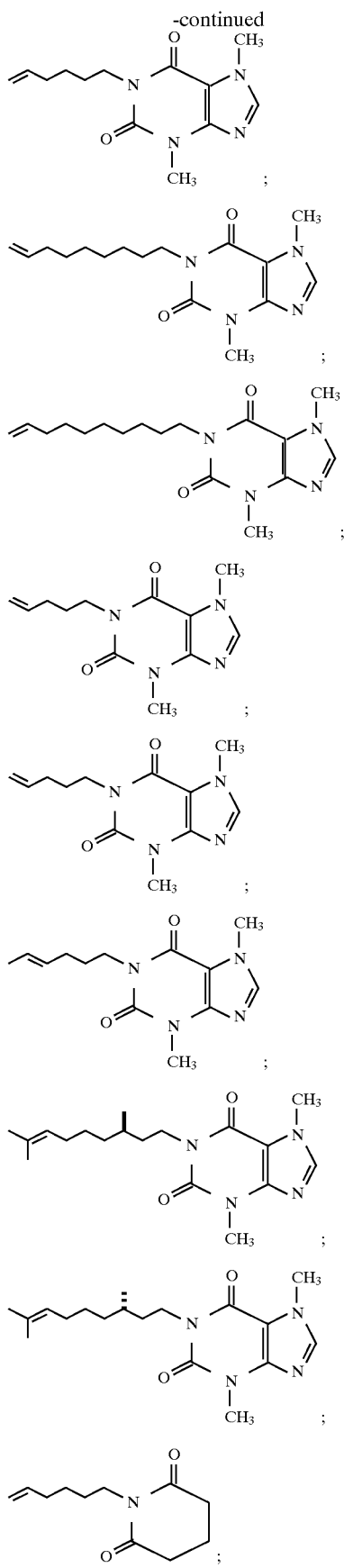

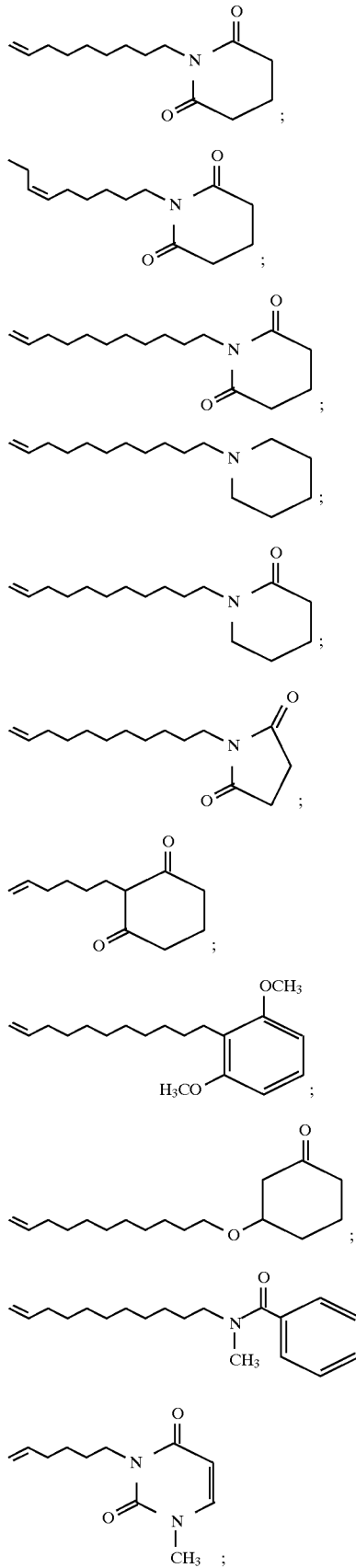
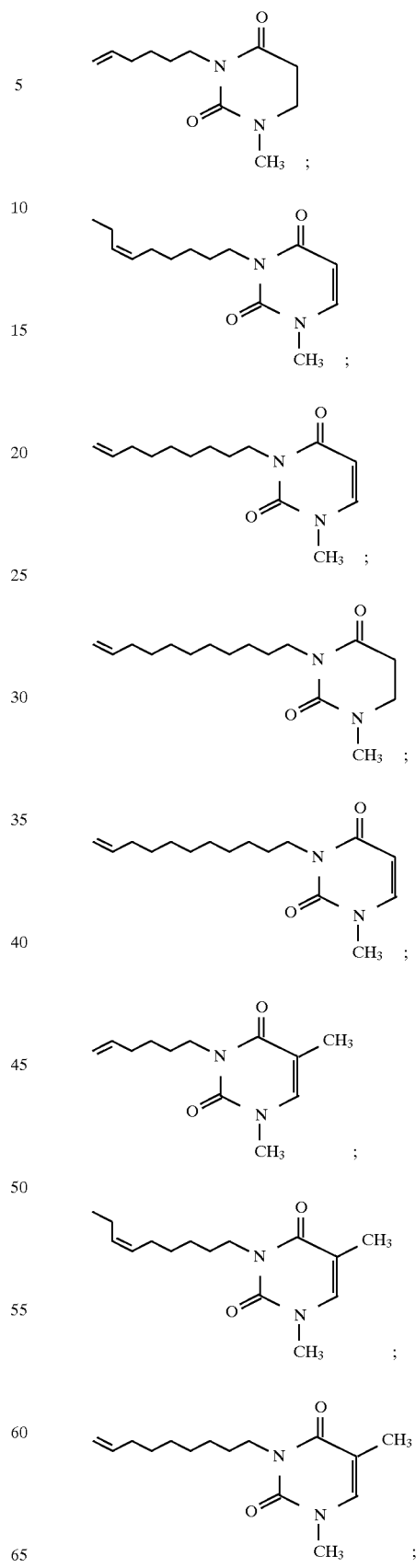

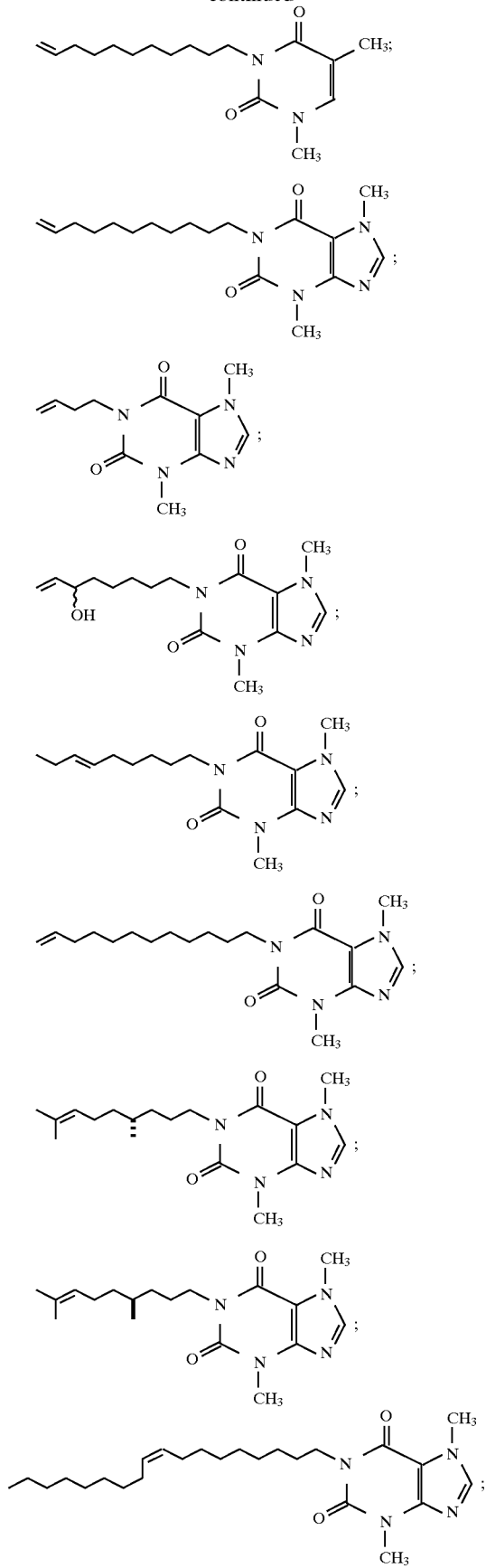
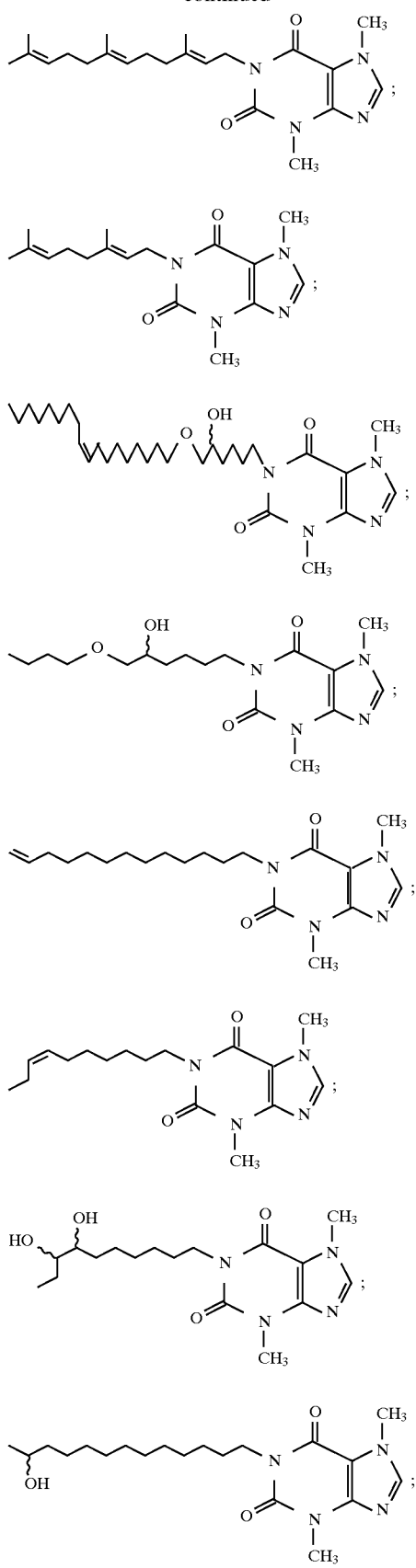

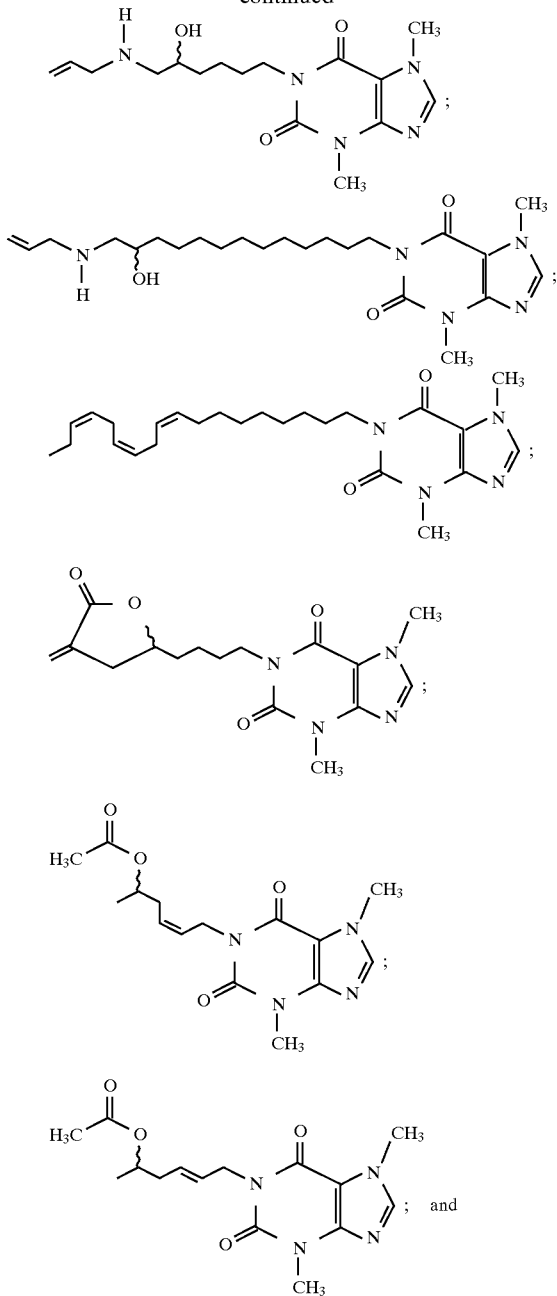

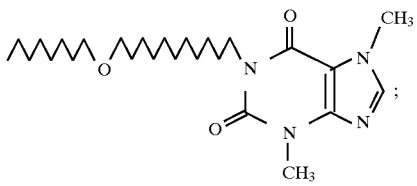

2. The method of claim 1 wherein:

the phosphatidic acid and diacylglycerol have at least one sn-1 or sn-2 acyl group; and at least one of the sn-1 or sn-2 acyl groups is saturated.

3. The method according to claim 1, wherein the sn-1 or sn-2 acyl group is selected from oleate, arachidonate, palmitate, myristate, and stearate.

4. The method according to claim 1, wherein phosphatidic acid and diacylglycerol are selected from the group consisting of 1-O-myristyl, 2-myristyl; 1,2-dimyristoyl; 1-O-palmitoyl, 2-oleoyl; 1-palmitoyl, 2-stearoyl; 1-palmitoyl, 2-oleoyl; 1-O-stearoyl, 2-oleoyl; 1,2-dioleoyl; 1-stearoyl, 2-arachidonyl; and 1-stearoyl, 2-oleoyl; 1-stearoyl, 2-oleoyl; 1-myristoyl, 2-oleoyl; 1-myristoyl, 2-palmitoyl; and 1-myristoyl, 2-stearoyl phosphatidic acid and diacylglycerol.

5. The method according to claim 1, wherein the allergic response is selected from the group consisting of asthma, rhinitis, urticaria, and eczema, chronic sinusitis, contact dermatitis, anaphylaxis, sting insect hypersensitivity, food allergies, allergic drug reaction, mastocytosis and angioedema.

6. The method according to claim 1, wherein inhibition of intracellular generation of PA and DAG lead to avoidance of early and late phase hypersensitivity of an allergic response.

7. The method according to claim 1, wherein early or late phase hypersensitivity is selected from the group consisting of degranulation and prostaglandin and leukotriene production.

* * * * *